US008481584B2

(12) United States Patent
Fancelli et al.

(10) Patent No.: US 8,481,584 B2
(45) Date of Patent: Jul. 9, 2013

(54) 1H-THIENO[2,3-C]PYRAZOLE DERIVATIVES USEFUL AS KINASE INHIBITORS

(75) Inventors: Daniele Fancelli, Milan (IT); Paola Vianello, Milan (IT); Mario Varasi, Milan (IT); Simona Bindi, Milan (IT); Sergio Vioglio, Cusano Milanino (IT); Dania Tesei, Ancona (IT)

(73) Assignee: Nerviano Medical Sciences S.R.L., Nerviano (MI) (IT)

(*) Notice: Subject to any disclaimer, the term of this patent is extended or adjusted under 35 U.S.C. 154(b) by 0 days.

(21) Appl. No.: 13/404,697

(22) Filed: Feb. 24, 2012

(65) Prior Publication Data
US 2012/0165311 A1    Jun. 28, 2012

Related U.S. Application Data

(62) Division of application No. 11/050,360, filed on Feb. 3, 2005, now Pat. No. 8,138,217.

(60) Provisional application No. 60/541,452, filed on Feb. 3, 2004.

(51) Int. Cl.
*A61K 31/4162* (2006.01)
*C07D 231/26* (2006.01)

(52) U.S. Cl.
USPC ...................................... 514/406; 548/360.5

(58) Field of Classification Search
USPC ....................................................... 514/406
See application file for complete search history.

(56) References Cited

U.S. PATENT DOCUMENTS

| 7,541,378 B2 | 6/2009 | Tonani et al. |
| 2005/0026984 A1 | 2/2005 | Bigot et al. |
| 2006/0122249 A1 | 6/2006 | Tonani et al. |

FOREIGN PATENT DOCUMENTS

| EP | 0 234 622 | 9/1987 |
| WO | WO 00/69846 | 11/2000 |
| WO | WO 01/12188 A1 | 2/2001 |
| WO | WO 01/12189 A1 | 2/2001 |
| WO | WO 02/12242 A2 | 2/2002 |
| WO | WO 02/48114 A1 | 6/2002 |
| WO | WO 02/070515 A2 | 9/2002 |
| WO | WO 03/028720 A1 | 4/2003 |
| WO | WO 03/097610 A1 | 11/2003 |
| WO | WO 2004/007504 A1 | 1/2004 |
| WO | WO 2004/013146 A1 | 2/2004 |

OTHER PUBLICATIONS

Meraldi P. et al., "Aurora Kinases Link Chromosome Segregation and Cell Division to Cancer Susceptibility", *Current Opinion in Genetics & Development*, 14:29-36 (2004).
Warner S.L. et al., "Targeting Aurora-2 Kinase in Cancer", *Molecular Cancer Therapeutics*, 2:589-595 (2003).
Sen S. et al., "Amplification/Overexpression of a Mitotic Kinase Gene in Human Bladder Cancer", *Journal of the National Cancer Institute*, 94(17):1320-1329 (2002).
Wilson K.J. et al., "Synthesis of Thiophene-2-Carboxamidines Containing 2-Amino-Thiazoles and Their Biological Evaluation as Urokinase Inhibitors", *Bioorganic & Medicinal Chemistry Letters*, 11:915-918 (2001).
Tanaka T. et al., "Centrosomal Kinase AIK1 is Overexpressed in Invasive Ductal Carcinoma of the Breast", *Cancer Research*, 59:2041-2044 (1999).
Cohen P., "The Development and Therapeutic Potential of Protein Kinase Inhibitors", *Current Opinion in Chemical Biology*, 3:459-465 (1999).
Sherif S.M. et al., "Syntheses with Heterocyclic β—Enaminonitriles: An Expeditious Synthetic Approach to Polyfunctionally Substituted 5-Phenyl-Sulfonylthiophenes and Their Fused Derivatives", *Monatshefte fur Chemie*, 128:687-696 (1997).
Isomers [online], [retrieved on Mar. 11, 2007] Retrieved from the Internet, URL: http://chemed.chem.purdue.edu/genchem/topicreview/bp/1organic/isomers.html.
Lala P.K. et al., "Role of Nitric Oxide in Tumor Progression: Lessons from Experimental Tumors", *Cancer and Metastasis Reviews* 17(1):91-106 (1998).
Golub T.R. et al., "Molecular Classification of Cancer: Class Discovery and Class Prediction by Gene Expression Monitoring", *Science* 286:531-537 (Oct. 15, 1999).
Cancer [online], [retrieved on Jul. 6, 2007] Retrieved from the Internet, URL; http://www.nlm.nih.gov/medlineplus/cancer.html.
Cancer [online], [retrieved on Jul. 6, 2007] Retrieved from the Internet, URL; http://en.wikipedia.org/wiki/Cancer.

*Primary Examiner* — Shawquia Young
(74) *Attorney, Agent, or Firm* — Scully, Scott, Murphy & Presser, P.C.

(57) ABSTRACT

Thieno[2,3-c]pyrazole derivatives of formula (I) and pharmaceutically acceptable salts thereof, as defined in the specification, process for their preparation and pharmaceutical compositions comprising them are disclosed; the compounds of the invention may be useful, in therapy, in the treatment of diseases associated with a disregulated protein kinase activity, like cancer.

4 Claims, No Drawings

1H-THIENO[2,3-C]PYRAZOLE DERIVATIVES USEFUL AS KINASE INHIBITORS

CROSS REFERENCE TO RELATED APPLICATIONS

The present application is a divisional of copending application Ser. No. 11/050,360 filed Feb. 3, 2005, which claims benefit of U.S. Provisional Application No. 60/541,452 filed Feb. 3, 2004, the entire contents of which are incorporated herein by reference.

BACKGROUND OF THE INVENTION

1. Field of the Invention

The present invention relates to thieno-pyrazole derivatives, to a process for their preparation, to pharmaceutical compositions comprising them, and to their use as therapeutic agents, particularly in the treatment of cancer and cell proliferation disorders.

2. Discussion of the Background

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, Current Opinion in Chemical Biology 1999, 3, 459-465.

Among the several protein kinases known in the art as being implicated in the growth of cancer cells are Aurora kinases, in particular Aurora-2.

Aurora-2 was found to be over-expressed in a number of different tumor types. Its gene locus maps at 20q13, a chromosomal region frequently amplified in many cancers, including breast [Cancer Res. 1999, 59(9), 2041-4] and colon.

20q13 amplification correlates with poor prognosis in patients with node-negative breast cancer and increased Aurora-2 expression is indicative of poor prognosis and decreased survival time in bladder cancer patients [J. Natl. Cancer Inst., 2002, 94(17), 1320-9]. For a general reference to Aurora-2 role in the abnormal centrosome function in cancer see also Molecular Cancer Therapeutics, 2003, 2, 589-595 and Curr. Opin. Genet. & Dev. 2004, 14(1), 29-36.

SUMMARY OF THE INVENTION

It is an object of the invention to provide compounds, which are useful in therapy as agents against a host of diseases caused by and/or associated to a disregulated protein kinase activity and, more particularly, Aurora kinases activity.

It is another object to provide compounds, which are endowed with protein kinase inhibiting activity and, more particularly, Aurora kinases inhibiting activity.

The present inventors have now discovered that some thieno-pyrazole compounds, and derivatives thereof, are endowed with protein kinase inhibiting activity, e.g. Aurora kinases inhibiting activity.

More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Due to the key role of PKs and Aurora kinases in the regulation of cellular proliferation, these thieno-pyrazole derivatives are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

Accordingly, in a first embodiment, the present invention provides a method for treating cell proliferative disorders caused by and/or associated with an altered protein kinase activity, which comprises administering to a mammal in need thereof an effective amount of a compound of formula (I)

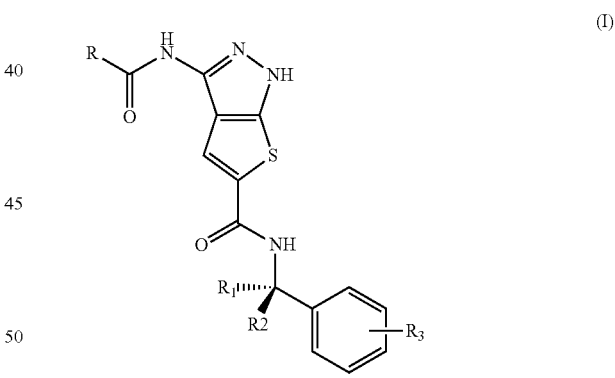

(I)

wherein

R is an optionally substituted aryl or heteroaryl group;

$R_1$ and $R_2$ represent, the same or different and independently from each other, a hydrogen atom, a straight or branched $C_1$-$C_3$ alkyl or a group —$CONH_2$ or —$CH_2NR'R''$ or, taken together with the carbon atom to which they are bonded, $R_1$ and $R_2$ may form a $C_3$-$C_6$ cycloalkyl group; with the proviso that at least one of $R_1$ and $R_2$ is other than a hydrogen atom; R' and R'' represent, the same or different and independently from each other, a hydrogen atom or a straight or branched $C_1$-$C_3$ alkyl group or, taken together with the nitrogen atom to which they are bonded, R' and R'' may form a heterocyclic ring of formula

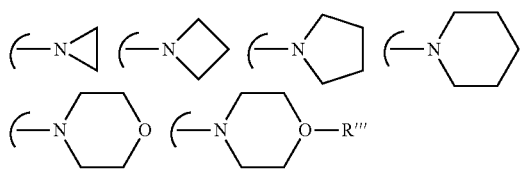 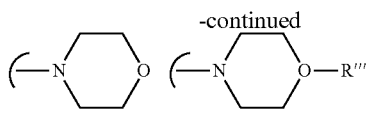

wherein R''' is a hydrogen atom or a straight or branched $C_1$-$C_3$ alkyl group;

$R_3$ is a hydrogen or halogen atom or a group selected from hydroxy, cyano, straight or branched $C_1$-$C_3$ alkyl or $C_1$-$C_3$ alkoxy;

or isomers, tautomers, carriers, metabolites, prodrugs, and pharmaceutically acceptable salts thereof.

The above method enables treatment of cell proliferative disorders caused by and/or associated with altered Aurora kinases activity. In a preferred embodiment of the method described above, the cell proliferative disorder is cancer.

Specific types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratoxanthoma, thyroid follicular cancer, and Kaposi's sarcoma.

The present invention also provides a compound of formula (I)

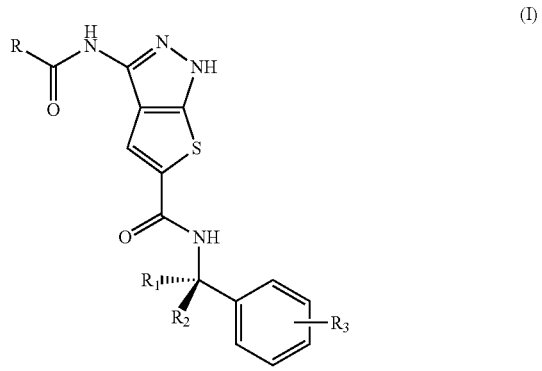

(I)

wherein

R is an optionally substituted aryl or heteroaryl group;

$R_1$ and $R_2$ represent, the same or different and independently from each other, a hydrogen atom, a straight or branched $C_1$-$C_3$ alkyl or a group —$CONH_2$ or —$CH_2NR'R''$ or, taken together with the carbon atom to which they are bonded, $R_1$ and $R_2$ may form a $C_3$-$C_6$ cycloalkyl group; with the proviso that at least one of $R_1$ and $R_2$ is other than a hydrogen atom; R' and R'' represent, the same or different and independently from each other, a hydrogen atom or a straight or branched $C_1$-$C_3$ alkyl group or, taken together with the nitrogen atom to which they are bonded, R' and R'' may form a heterocyclic ring of formula

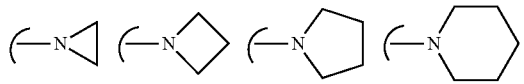

wherein R''' is a hydrogen atom or a straight or branched $C_1$-$C_3$ alkyl group;

$R_3$ is a hydrogen or halogen atom or a group selected from hydroxy, cyano, straight or branched $C_1$-$C_3$ alkyl or $C_1$-$C_3$ alkoxy;

or isomers, tautomers, carriers, metabolites, prodrugs, and pharmaceutically acceptable salts thereof.

The present invention also includes methods of synthesizing the thieno-pyrazole compounds of formula (I) and the pharmaceutically acceptable salts, as well as the pharmaceutical compositions comprising them.

A more complete appreciation of the invention and many of the attendant advantages thereof will be readily obtained as the same becomes better understood by reference to the following detailed description.

DETAILED DESCRIPTION OF THE INVENTION

Several heterocyclic compounds are known in the art as protein kinase inhibitors. As an example, 2-carboxamido-pyrazole and 2-ureido-pyrazole derivatives have been disclosed as protein kinase inhibitors in the international patent applications WO 01/12189, WO 01/12188, WO 02/48114 and WO 02/70515, all in the name of the applicant itself. Fused bicyclic compounds comprising pyrazole moieties and possessing kinase inhibitory activity have been also disclosed in WO 00/69846, WO 02/12242, WO 03/028720, WO 03/097610 as well as in WO2004007504 and WO2004013146 applications (respectively claiming priority from U.S. 60/396,174 of Jul. 17, 2002; and U.S. 60/398,121 of Jul. 25, 2002) all in the name of the applicant itself.

In addition, 5-phenylsulfonyl-thieno[2,3-c]pyrazole derivatives are also known in the art as synthetic intermediates for the preparation of more complex heterocyclic structures, as reported in Monatshefte fur Chemie 128, 687-696 (1997).

The compounds of the present invention fall within the scope of the general formula of the aforementioned WO2004013146 but are not specifically exemplified therein.

The compounds of formula (I) of the invention have asymmetric carbon atoms and may therefore exist as individual optical isomers, as racemic mixtures or as any other mixture comprising a majority of one of the two optical isomers, which are all to be intended as within the scope of the present invention.

Likewise, the use as an antitumor agent of all the possible isomers and their admixtures and of both the metabolites and the pharmaceutically acceptable bio-precursors (otherwise referred to as pro-drugs) of the compounds of formula (I) are also within the scope of the present invention.

Prodrugs are any covalently bonded compounds, which release the active parent drug, according to formula (I), in vivo.

In cases when compounds may exist in tautomeric forms, each form is contemplated as being included within this invention whether existing in equilibrium or predominantly in one form.

As such, unless otherwise provided, when only one of the following tautomeric forms of formula (Ia) or (Ib) is indicated, the remaining one has still to be intended as comprised within the scope of the invention:

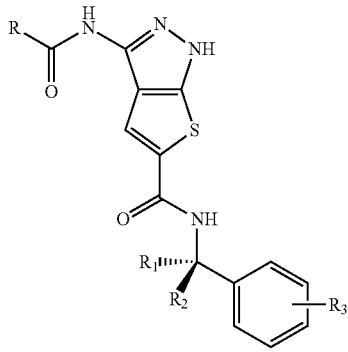

(Ia)

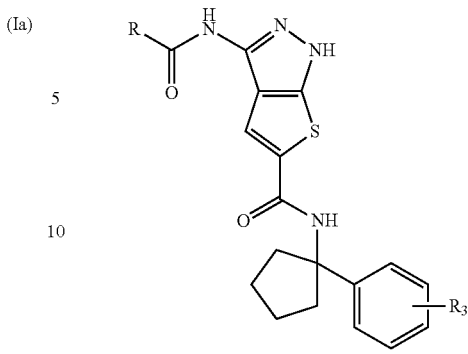

(Ib)

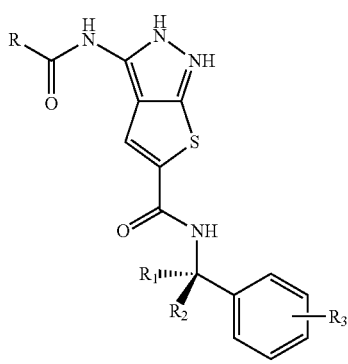

In the present description, unless otherwise specified, with the term aryl group we intend any aromatic carbocyclic ring system of 1 or 2 ring moieties, either fused or linked to each other through a single bond, for instance including phenyl, □- or □-naphthyl or biphenyl groups.

With the term heteroaryl we intend any aromatic heterocyclic ring which may comprise an optionally benzocondensed 5 or 6 membered heterocycle with from 1 to 3 heteroatoms selected among N, O or S.

Non limiting examples of heteroaryl groups according to the invention may thus include, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, and the like.

With the term straight or branched $C_1$-$C_3$ alkyl or $C_1$-$C_3$ alkoxy we intend any of the groups such as methyl, ethyl, n-propyl, isopropyl, methoxy, ethoxy, n-propoxy and isopropoxy.

With the term halogen atom we intend a fluorine, chlorine, bromine or iodine atom. With the term $C_3$-$C_6$ cycloalkyl we intend any group such as cyclopropyl, cyclobutyl, cyclopentyl or cyclohexyl.

Clearly, as these same cycloalkyl groups may be formed when $R_1$ and $R_2$ are taken together with the carbon atom to which they are attached, cyclic spiro compounds may be thus obtained. Just as an example, when $R_1$ and $R_2$ together form a cyclopentyl group, derivatives having the following general formula are herewith considered:

When considering derivatives of formula (I) wherein $R_1$ or $R_2$ represents a group —$CH_2NR'R''$ and R' and R'' are linked together with the nitrogen atom to which they are attached, heterocyclic moieties may be thus formed as per the general formula. Just as an example, by considering $R_1$ as hydrogen and $R_2$ as a group —$CH_2NR'R''$ with R' and R'' linked together so as to form a pyrrolidinyl-1-yl group, compounds having the following general formula are herewith considered:

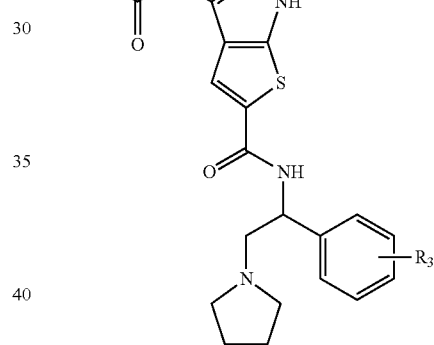

From all of the above, it is clear to the skilled man that the compounds of formula (I) of the invention are characterized by the presence of a moiety, hereinafter simply referred to as benzylamino moiety, wherein the methylene group is necessarily substituted by at least one of the groups $R_1$ and $R_2$ which is different from hydrogen.

According to the meanings provided to R, any of the above aryl or heteroaryl groups may be optionally further substituted in any of their free positions by one or more groups, for instance 1 to 6 groups, selected from: halogen, nitro, carboxy, cyano, alkyl, polyfluorinated alkyl, alkenyl, alkynyl, cycloalkyl, cycloalkenyl; aryl, heterocyclyl, alkyl-heterocyclyl, heterocyclyl-alkyl, amino-alkyl, amino groups and derivatives thereof such as, for instance, alkylamino, dialkylamino, arylamino, diarylamino, ureido, alkylureido or arylureido; carbonylamino groups and derivatives thereof such as, for instance, formylamino, alkylcarbonylamino, alkenylcarbonylamino, arylcarbonylamino, alkoxycarbonylamino; hydroxy groups and derivatives thereof such as, for instance, alkoxy, polyfluorinated alkoxy, aryloxy, heterocylyloxy, alkylcarbonyloxy, arylcarbonyloxy, cycloalkenyloxy or alkylideneaminoxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulfonyl, arylsulfonyl, alkylsulfinyl, arylsulfinyl, arylsulfonyloxy, aminosulfonyl, alkylaminosulfonyl or dialkylaminosulfonyl.

In their turn, whenever appropriate, each of the above substituents may be further substituted by one or more of the aforementioned groups.

With the term alkyl or alkoxy group we intend, unless otherwise provided, any straight or branched $C_1$-$C_6$ alkyl or alkoxy group, hence comprehensive of the aforementioned $C_1$-$C_3$ alkyl or alkoxy groups and also comprising n-butyl, iso-butyl, sec-butyl, tert-butyl, n-pentyl, n-hexyl, n-butoxy, iso-butoxy, sec-butoxy, tert-butoxy, n-pentyloxy, n-hexyloxy, and the like.

With the term alkenyl or alkynyl group we intend, unless otherwise provided, any unsaturated straight or branched $C_2$-$C_6$ alkenyl or alkynyl group such as, for instance, vinyl, allyl, 1-propenyl, isopropenyl, 1-, 2- or 3-butenyl, pentenyl, hexenyl, ethynyl, 1- or 2-propynyl, butynyl, pentynyl, hexynyl, and the like.

With the term polyfluorinated alkyl or alkoxy we intend any straight or branched $C_1$-$C_6$ alkyl or alkoxy group as above defined, wherein more than one hydrogen atom is replaced by fluorine atoms such as, for instance, trifluoromethyl, trifluoromethoxy, 2,2,2-trifluoroethyl, 2,2,2-trifluoroethoxy, 1,2-difluoroethyl, 1,1,1,3,3,3-hexafluoropropyl-2-yl, and the like.

With the term heterocycle, heterocyclyl or heterocyclic group we also intend an optionally benzocondensed 4 to 7 membered heterocycle, hence encompassing aromatic heterocyclic groups also known as heteroaryl groups, either saturated or partially unsaturated, with from 1 to 3 heteroatoms selected among N, O and S.

Examples of these 4 or 7 membered heterocyclic groups are, for instance, 1,3-dioxolane, pyran, pyrrolidine, pyrroline, imidazoline, imidazolidine, pyrazolidine, pyrazoline, piperidine, piperazine, morpholine, tetrahydrofuran, hexamethyleneimine, 1,4-hexahydrodiazepine, azetidine, and the like.

With the term cycloalkenyl we intend any of the aforementioned $C_3$-$C_6$ cycloalkyl groups further comprising a double bond such as, for instance, 2-cyclopenten-1-yl, 3-cyclopenten-1-yl, 1-cyclohexen-1-yl, 2-cyclohexen-1-yl, 3-cyclohexen-1-yl, and the like.

From all of the above, it is clear to the skilled man that any group which name has been identified as a composite name such as, for instance, cycloalkylalkyl, arylalkyl, heterocyclylalkyl, alkylthio, aryloxy, arylalkyloxy, alkylcarbonyloxy and the like, has to be intended as conventionally construed from the parts to which they derive. So far, as an example, the term alkoxy-heterocyclyl-alkyl stands for a straight or branched alkyl group substituted by a heterocycle further substituted by alkoxy, wherein alkyl, heterocycle and alkoxy are as above defined. Likewise, the term alkyl-heterocyclyloxy stands for a heterocyclyloxy group further substituted by alkyl.

The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of the compounds of the present invention may be prepared from an inorganic or organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, arylaliphatic, heterocyclic, carboxylic and sulfonic classes of organic acids, examples of which are formic, acetic, trifluoroacetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, hydroxybutyric, galactaric and galacturonic acid. Suitable pharmaceutically acceptable base addition salts of the compounds of the present invention include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methyl-glucamine) and procaine. All of these salts may be prepared by conventional means from the corresponding compounds of the present invention, for instance by reacting them with the appropriate acid or base.

A preferred class of compounds of the invention is represented by the derivatives of formula (I) wherein R is a group, optionally further substituted, selected from thienyl, furyl, pyrrolyl and phenyl.

More preferably, within the above class, are the derivatives of formula (I) wherein R is thienyl, furyl, pyrrolyl, N-methyl-pyrrolyl, phenyl and phenyl substituted by halogen atoms, heterocycles, amino-alkyl groups, heterocylyloxy or heterocyclylalkyl groups. Even more preferably, within the above class of compounds of formula (I), R is selected from 2-thienyl, 2-furyl, 1-methyl-pyrrolyl-2-yl, phenyl, 4-fluorophenyl, 4-(1-methyl-piperidyl-4-yloxy)phenyl, 4-(1-methyl-piperazinyl-4-yl)phenyl, 4-(1-methyl-piperazinyl-4-yl-methyl)phenyl 4-(pyrrolidin-1-yl)methyl-phenyl, 4-(piperidin-1-yl)methyl-phenyl, 4-(1-methyl-piperazin-4-yl)methyl-phenyl, 4-(morpholino-1-yl)methyl-phenyl, 4-(alkylamino)methyl-phenyl, 4-(dialkylamino)methyl-phenyl or 4-(morpholino-4-yl)phenyl.

Another preferred class of compounds of the invention is represented by the derivatives of formula (I) wherein one of $R_1$ and $R_2$ is a hydrogen atom or a methyl group and the remaining one of $R_1$ and $R_2$ is methyl, ethyl or a group —$CH_2NR'R''$ wherein R' and R" are as set forth above.

Another preferred class of compounds of the invention is represented by the derivatives of formula (I) wherein $R_1$ and $R_2$, together with the carbon atom to which they are attached, form a $C_3$-$C_6$ cycloalkyl group and, even more preferably, cyclopropyl or cyclopentyl.

Another preferred class of compounds of the invention is represented by the derivatives of formula (I) wherein R, $R_1$ and $R_2$ are as set forth above and $R_3$ represents a hydrogen, fluorine or chlorine atom, or a group selected from hydroxy, methoxy or cyano.

For a reference to any specific compound of formula (I) of the invention, optionally in the form of a pharmaceutically acceptable salt, see the following experimental section.

As formerly indicated, a further object of the present invention is represented by the process for preparing the compounds of formula (I) and the pharmaceutically acceptable salts thereof, which process comprises:

a) reacting a compound of formula (II), wherein Alk stands for a lower alkyl group, with hydrazine or a hydrazine salt and reacting the thus obtained intermediate compound under acidic conditions so as to obtain a compound of formula (III)

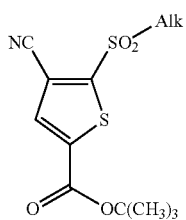

(II)

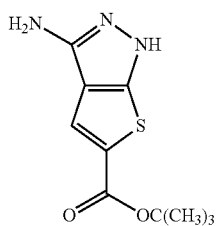

(III)

(b) reacting the compound of formula (III) with any suitable pyrazole nitrogen atom protecting agent, so as to obtain a compound of formula (IV), in any one of its tautomeric forms (IVa) or (IVb)

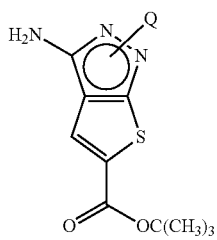

(IV)

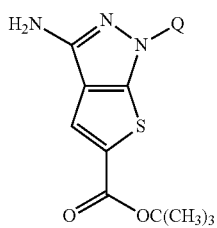

(IVa)

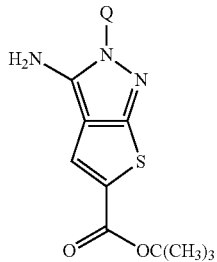

(IVb)

and wherein Q represents the said protecting group;

c) acylating the compound of formula (IV) with a compound of formula (V), wherein R is as set forth above and Z represents a suitable leaving group, so as to obtain a compound of formula (VI)

R—COZ (V)

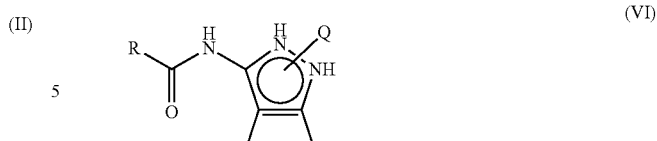

(VI)

d) selectively hydrolyzing the tert-butyl ester group so as to obtain a compound of formula (VII)

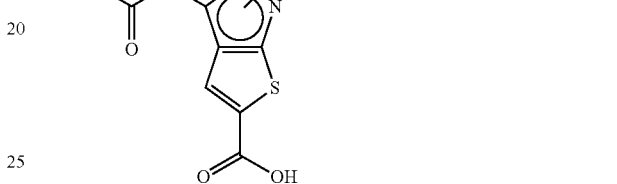

(VII)

e) reacting the compound of formula (VII) with a compound of formula (VIII) wherein $R_1$, $R_2$ and $R_3$ are as set forth above, in the presence of any suitable condensing agent, so as to obtain a compound of formula (IX)

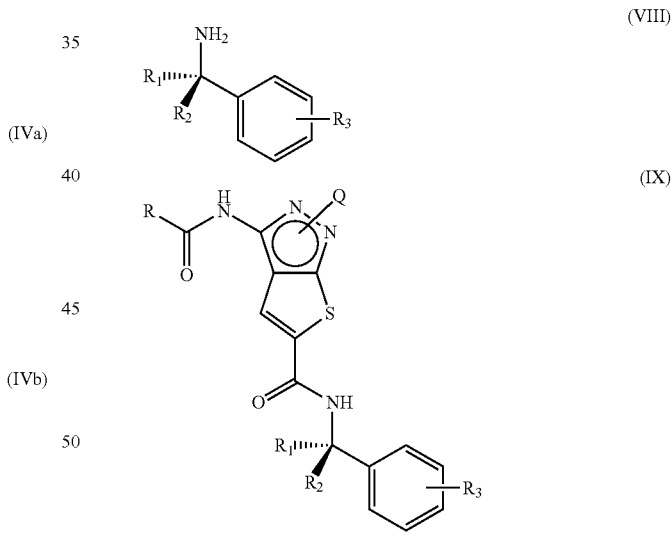

(VIII)

(IX)

f) deprotecting the compound of formula (IX) from the Q pyrazole nitrogen atom protecting group so as to obtain the compound of formula (I) and, whenever desired, converting the compound of formula (I) into a pharmaceutically acceptable salt or converting the salt thereof into the free compound of formula (I).

A compound of formula I wherein R is an optionally substituted 4'-(amino-methyl)phenyl group can be optionally prepared by:

f') treating derivatives of formula IX, wherein R is a phenyl group substituted at position 4' with a chloromethyl group with ammonia or a primary or secondary amine to deprotect and convert them into a compound of formula I, wherein R is an optionally substituted 4'-(amino-methyl)phenyl group, as shown in the following scheme:

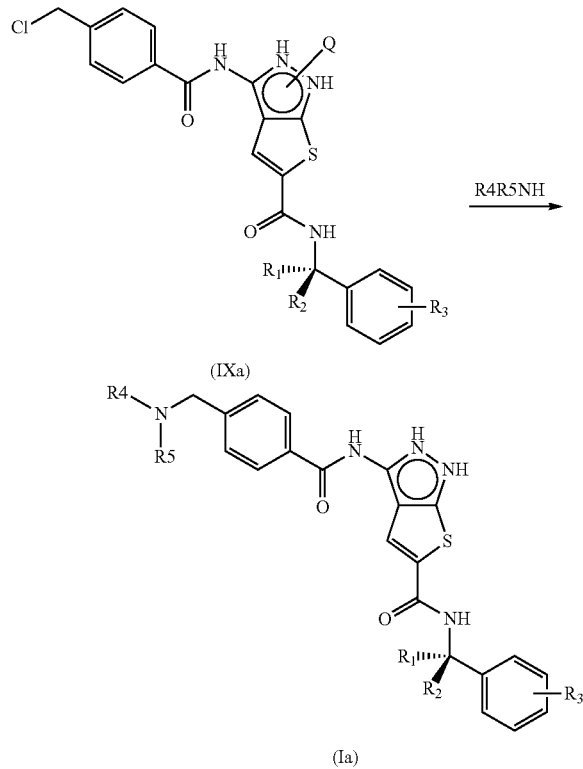

The above process is an analogy process, which can be carried out according to methods known in the art.

From the above, it is clear to the person skilled in the art that if a compound of formula (I), prepared according to the above process, is obtained as an admixture of isomers, their separation into the single isomers of formula (I), carried out according to conventional techniques, is still within the scope of the present invention.

According to step (a) of the process, the reaction between a compound of formula (II) and hydrazine or a hydrazine salt, for instance hydrazine dihydrochloride or hydrazine sulphate or acetate, can be carried out in the presence of catalytic amounts of an acid such as hydrochloric, acetic or sulphuric acid, or in the presence of catalytic amounts of a Lewis acid such as boron trifluoride dimethyl etherate. Alternatively, this same reaction may be also accomplished in the presence of catalytic amounts of a strong base such as sodium methoxide.

The reaction is carried out in a suitable solvent such as, for instance, N,N'-dimethylformamide, tetrahydrofuran, 1,4-dioxane, acetonitrile, water, methanol or ethanol, at a temperature ranging from about room temperature to reflux and for a time varying from about 30 minutes to about 18 hours.

According to a preferred embodiment, within the compounds of formula (II), Alk represents a straight or branched lower alkyl group, for instance a $C_1$-$C_6$ alkyl group and even more preferably a $C_1$-$C_4$ alkyl group.

Preferably, step (a) is carried out by reacting a compound of formula (II) with hydrazine hydrate in methanol, ethanol or tetrahydrofuran at a temperature ranging from room temperature to refluxing temperature. The obtained tert-butyl 4-cyano-5-hydrazinothiophene-2-carboxylate intermediate can be either separated from the reaction medium and further processed as per the working examples or, alternatively, directly processed through cyclization so as to afford the compound of formula (III). Cyclization is carried out at a temperature ranging from about 15° C. to about 50° C. in methanol or ethanol, and in the presence of catalytic amounts of a mineral acid such as hydrochloric or sulphuric acid.

According to step (b) of the process, the thus obtained thieno-pyrazole derivative of formula Op is then protected, according to well-known methods, at the pyrazole nitrogen atom. As an example, the above protection may occur with an alkyl chlorocarbonate, in a suitable solvent such as tetrahydrofuran, dichloromethane, chloroform, acetonitrile, toluene or mixtures thereof, at a temperature ranging from about −5° C. to about 35° C. and for a time varying from about 30 minutes to about 72 hours, in the presence of an opportune proton scavenger such as triethylamine or diisopropylethylamine.

According to step (c) of the process, the compound of formula (IV) is then reacted with any suitable acylating agent of formula (V) so as to yield the compound of formula (VI), by working according to methods well known in the art for the preparation of carboxamido derivatives. Typically, within the compound of formula (V), Z represents a halogen atom and, even more preferably, a bromine or chlorine atom.

The reaction is carried out in a suitable solvent such as, for instance, tetrahydrofuran, dimethylformamide, dichloromethane, chloroform, acetonitrile, toluene or mixtures thereof, at a temperature ranging from about −10° C. to reflux and for a time varying from about 30 minutes to about 96 hours, in the presence of an opportune proton scavenger such as triethylamine, N,N-diisopropylethylamine or pyridine.

From the above, it is clear to the skilled person that the above protection at the pyrazole nitrogen atom, in step (b), is of particular advantage as it prevents that acylation with the compound of formula (V), in step (c), occurs at the pyrazole nitrogen atom. According to step (d) of the process, the carboxyester function of the compound of formula (VII) is selectively hydrolized so as to yield the corresponding carboxy group.

The reaction is carried out under acidic conditions, preferably in the presence of hydrochloric acid in dioxane, by operating at room temperature and for a suitable time, for instance up to 72 hours.

According to step (e) of the process, the compound of formula (VII) is then reacted with a suitable amino derivative of formula (VIII) so as to lead to the corresponding compound of formula (IX).

From the above it is clear to the skilled person that this reaction may be accomplished in a variety of ways and operative conditions, which are widely known in the art for the preparation of carboxamides.

As an example, the reaction between the compounds of formula (VII) and (VIII) can be carried out in the presence of a coupling agent such as, for instance, 2-(1H-benzotriazol-1-yl)-1,1,3,3-tetramethyluronium tetrafluoroborate (TBTU), 1,3-dicyclohexylcarbodiimide, 1,3-diisopropylcarbodiimide, 1-(3-dimethylaminopropyl)-3-ethylcarbodiimide, N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene, or N,N-dimethylformamide at a temperature ranging from about
−10° C. to reflux and for a suitable time, for instance from about 30 minutes to about 96 hours. The said reaction is optionally carried out in the presence of a suitable catalyst, for instance 4-dimethylaminopyridine, or in the presence of a further coupling reagent such as N-hydroxybenzotriazole.

Alternatively, this same reaction can be also carried out, for example, through a mixed anhydride method, by using an alkyl chloroformate such as ethyl, iso-butyl, or iso-propyl chloroformate, in the presence of a tertiary base such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about −30° C. to room temperature.

According to step (f) of the process, the compound of formula (IX) is deprotected at the pyrazole nitrogen atom under basic conditions and by working according to conventional techniques, for instance by treatment with aqueous sodium or potassium hydroxide in the presence of a suitable co-solvent such as methanol, ethanol, dimethylformamide, 1,4-dioxane, or by treatment with a tertiary amine such as triethylamine or N,N-diisopropylethylamine and by using an alcohol like methanol or ethanol as the solvent. Deprotection may occur at a temperature ranging from about 18° C. to refluxing temperature of the solvent, for a time varying from about 30 minutes to about 72 hours.

Finally, according to step f') of the process, the benzylic chlorine atom of the compound of formula (IXa) is substituted by treatment with ammonia or a primary or secondary amine in a suitable solvent like as methanol, ethanol, tetrahydrofuran, dimethylformamide, at a temperature ranging from 0° C. to the reflux temperature of the solvent. In these conditions the simultaneous removal of the protecting group at the pyrazole nitrogen also occurs.

If desired, the salification of a compound of formula (I) or the conversion of a corresponding salt thereof into the free compound (1), according to step (f) of the process, can be easily carried out according to well-known methods in the art.

As it will be appreciated by the person skilled in the art, when preparing the compounds of formula (I) object of the invention, optional functional groups within both the starting materials or the intermediates thereof and which could give rise to unwanted side reactions, need to be properly protected according to conventional techniques. Likewise, the conversion of these latter into the free deprotected compounds may be carried out according to known procedures.

So far, when the thieno-pyrazole derivative of the process being protected at the pyrazole nitrogen atom is properly functionalized through carboxamido formation, in steps (c) and (e) of the process, the subsequent deprotection may occur under mild operative conditions, hence allowing to obtain the desired compound of formula (I).

Whenever desired, according to an alternative embodiment of the invention, the compound of formula (III) of step (a) may be reacted with an excess of the compound of formula (V), by working as reported in step (c), so as to get the desired functionalization at the amino moiety and, in the meantime, the protection at the pyrazole nitrogen atom.

Therefore, it is a further object of the invention a process for preparing the compounds of formula (I) and the pharmaceutically acceptable salts thereof, which process comprises:

a') reacting the compound of formula (III) being obtained in step (a) of the process with an excess of a compound of formula (V), wherein R is as set forth above and Z represents a suitable leaving group, so as to obtain a compound of formula (X)

R—COZ (V)

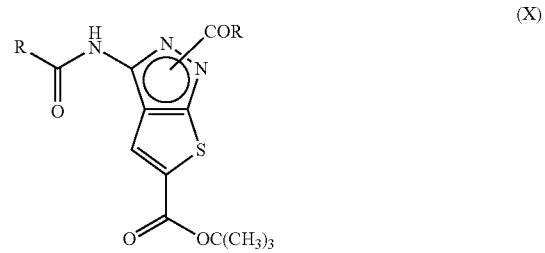

b') deprotecting the compound of formula (X) at the pyrazole nitrogen atom, as per step (f) of the process, and further reacting the resultant compound according to the remaining steps (d) and (e).

All of the compounds of formula (II), (V) and (VIII) are known or can be obtained according to known methods.

As an example, the starting material of formula (II) wherein Alk stands for methyl can be easily obtained as follows, by starting from commercially available ethyl 4-cyano-5-(methylthio)thiophene-2-carboylate:

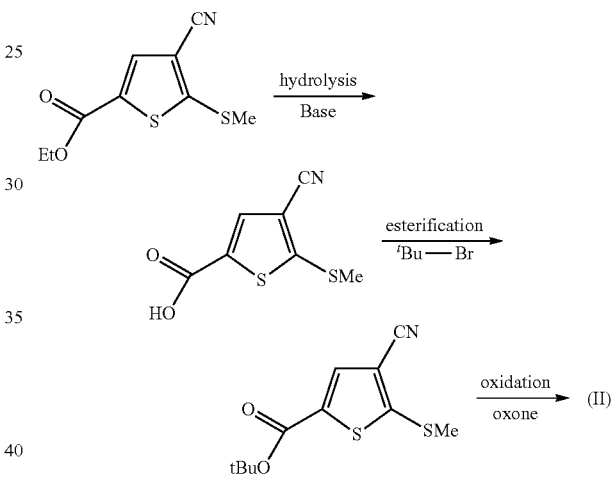

The hydrolysis of the ethoxycarbonyl group is carried out according to well-known methods, for instance in the presence of aqueous alkaline solutions such as aqueous sodium hydroxide.

Likewise, esterification is carried out according to well-known operative conditions, in the presence of an alkylating agent like tert-butyl bromide or di-tertbutyl-dicarbonate, in a suitable solvent such as dimethylformamide or tetrahydrofuran.

Finally, the conversion of the alkylthio group into alkylsulfonyl can be carried in the presence of any opportune oxidizing agent such as, for instance, hydrogen peroxide, 3-chloroperoxybenzoic acid or oxone, in a suitable solvent such as, for instance, dichloromethane, DMF, acetone, toluene, acetonitrile, methanol, ethanol, water, acetic acid, at a temperature ranging from about −10° C. to reflux and for a time varying from about 30 minutes to about 4 days.

For a general reference to the preparation of the compounds of formula (II) see, as an example, J. Bioorg. Med. Chem. Lett. 11 (2001), 915-918; EP-A-234622; as well as the following experimental section.

Pharmacology

The compounds of formula (I) are active as protein kinase inhibitors, more particularly as Aurora kinases inhibitors and are therefore useful, for instance, to restrict the unregulated proliferation of tumor cells.

In therapy, they may be used in the treatment of various tumors, such as those formerly reported, as well as in the treatment of other cell proliferative disorders such as psoriasis, vascular smooth cell proliferation associated with atherosclerosis and post-surgical stenosis and restenosis.

The inhibiting activity and the potency of selected compounds is determined through a method of assay based on the use of the SPA technology (Amersham Pharmacia Biotech).

The assay consists of the transfer of radioactivity labelled phosphate moiety by the kinase to a biotinylated substrate. The resulting 33P-labelled biotinylated product is allowed to bind to streptavidin-coated SPA beads (biotin capacity 130 pmol/mg), and light emitted was measured in a scintillation counter.

Inhibition Assay of Aurora-2 Activity

Kinase reaction: 8 µM biotinylated peptide (4 repeats of LRRWSLG), 10 µM ATP (0.5 uCi $P^{33}\gamma$-ATP), 7.5 ng Aurora 2, inhibitor in a final volume of 30 µl buffer (HEPES 50 mM pH 7.0, $MgCl_2$ 10 mM, 1 mM DTT, 0.2 mg/mL BSA, 3 µM orthovanadate) were added to each well of a 96 U bottom well plate. After 60 minutes at room temperature incubation, reaction was stopped and biotinylated peptide captured by adding 100 µl of bead suspension.

Stratification: 100 µl of CsCl2 5 M were added to each well and let stand 4 hour before radioactivity was counted in the Top-Count instrument.

IC50 determination: inhibitors were tested at different concentrations ranging from 0.0015 to 10 µM. Experimental data were analyzed by the computer program GraphPad Prizm using the four parameter logistic equation:

$$y=\text{bottom}+(\text{top}-\text{bottom})/(1+10^{((\log IC50-x)*\text{slope})})$$

where x is the logarithm of the inhibitor concentration, y is the response; y starts at bottom and goes to top with a sigmoid shape.

Ki Calculation:

Experimental method: Reaction was carried out in buffer (10 mM Tris, pH 7.5, 10 mM $MgCl_2$, 0.2 mg/mL BSA, 7.5 mM DTT) containing 3.7 nM enzyme, histone and ATP (constant ratio of cold/labeled ATP 1/3000). Reaction was stopped with EDTA and the substrate captured on phosphomembrane (Multiscreen 96 well plates from Millipore). After extensive washing, the multiscreen plates were read on a top counter. Control (time zero) for each ATP and histone concentrations was measured.

Experimental design: Reaction velocities are measured at four ATP, substrate (histone) and inhibitor concentrations. An 80-point concentration matrix was designed around the respective ATP and substrate Km values, and the inhibitor IC50 values (0.3, 1, 3, 9 fold the Km or IC50 values). A preliminary time course experiment in the absence of inhibitor and at the different ATP and substrate concentrations allows the selection of a single endpoint time (10 min) in the linear range of the reaction for the Ki determination experiment.

Kinetic parameter estimates: Kinetic parameters were estimated by simultaneous nonlinear least-square regression using [Eq.1] (competitive inhibitor respect to ATP, random mechanism) using the complete data set (80 points):

$$v = \frac{Vm \cdot A \cdot B}{\alpha \cdot Ka \cdot Kb + \alpha \cdot Ka \cdot B + \alpha \cdot Kb \cdot A + A \cdot B + \alpha \cdot \frac{Ka}{Ki} \cdot I \cdot \left(Kb + \frac{B}{\beta}\right)} \quad [\text{Eq. 1}]$$

where A=[ATP], B=[Substrate], I=[inhibitor], Vm=maximum velocity, Ka, Kb, Ki the dissociation constants of ATP, substrate and inhibitor respectively. α and β the cooperativity factor between substrate and ATP binding and substrate and inhibitor binding respectively.

The compounds of the invention were further tested, in vitro, to assess the anti-proliferative effect onto cell cultures.

In Vitro Cell Proliferation Assay

The human colon cancer cell line HCT-116 was seeded at 5000 cells/cm2 in 24 wells plate (Costar) using F12 medium (Gibco) supplemented with 10% FCS (EuroClone, Italy) 2 mM L-glutamine and 1% penicillin/streptomycin and maintained at 37° C., 5% $CO_2$ and 96% relative humidity. The following day, plates were treated in duplicates with 5 ul of an appropriate dilution of compounds starting from a 10 mM stock in DMSO. Two untreated control wells were included in each plate. After 72 hours of treatment, medium was withdrawn and cells detached from each well using 0.5 mL of 0.05% (w/v) Trypsin, 0.02% (w/v) EDTA (Gibco). Samples were diluted with 9.5 mL of Isoton (Coulter) and counted using a Multisizer 3 cell counter (Beckman Coulter). Data were evaluated as percent of the control wells:

% of CTR=(Treated−Blank)/(Control−Blank).

$IC_{50}$ values were calculated by LSW/Data Analysis using Microsoft Excel sigmoidal curve fitting.

Given the above assays, the compounds of formula (I) of the invention resulted to possess a remarkable protein kinase inhibitory activity, e.g. Aurora-2 inhibitory activity. See, as an example, the following table I reporting the experimental data of some representative compounds of the invention being tested as Aurora-2 kinase inhibitors ($IC_{50}$ nM) and for their cell antiproliferative effect ($IC_{50}$ nM).

Interestingly, these same derivatives were tested in comparison to a structurally very close compound, herewith defined as Reference compound, which is specifically disclosed in the aforementioned PCT/EP03/07531 patent application—see compound No. 421 of example 6.

Reference compound

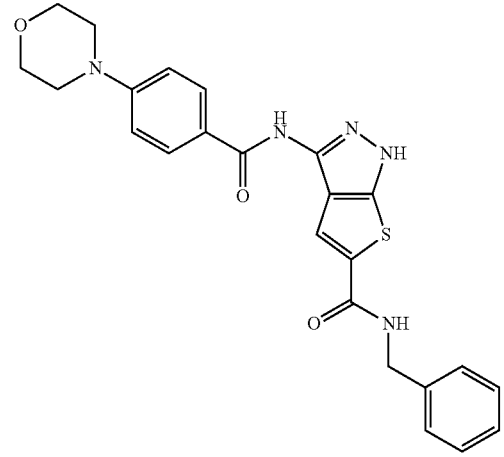

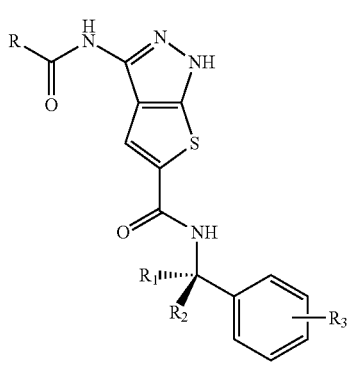

Reference Compound: N-benzyl-3-[(4-morpholin-4-yl-benzoyl)amino]-1H-thieno[2,3-c]pyrazole-5-carboxamide;

Compound (1) [R=4-(morpholinyl-4-yl)phenyl; $R_1=R_2$=methyl; $R_3$=H]: N-(1-methyl-1-phenylethyl)-3-[(4-morpholin-4-ylbenzoyl)amino]-1H-thieno[2,3-c]pyrazole-5-carboxamide;

Compound (2) [R=4-(morpholinyl-4-yl)phenyl; $R_1$ and $R_2$ together=—$CH_2$—$CH_2$—; $R_3$=H]: 3-[(4-morpholin-4-yl-benzoyl)amino]-N-(1-phenylcyclopropyl)-1H-thieno[2,3-c]pyrazole-5-carboxamide;

Compound (3) [R=4-(morpholinyl-4-yl)phenyl; $R_1$=methyl; $R_2$=H; $R_3$=F]: N-[(1R)-1-(4-fluorophenyl)ethyl]-3-[(4-morpholin-4-ylbenzoyl)amino]-1H-thieno[2,3-c]pyrazole-5-carboxamide;

Compound (5) [R=4-(morpholinyl-4-yl)phenyl; $R_1$=(pyrrolidinyl-1-yl)methyl; $R_2=R_3$=H]: 3-[(4-morpholin-4-yl-benzoyl)amino]-N-[(1S)-1-phenyl-2-pyrrolidin-1-ylethyl]-1H-thieno[2,3-c]pyrazole-5-carboxamide;

Compound (29) [R=4-(4-methyl-piperazinyl-1-yl)phenyl; $R_1=R_2$=methyl; $R_3$=H]: N-(1-methyl-1-phenylethyl)-3-{[4-(4-methylpiperazin-1-yl)benzoyl]amino}-1H-thieno[2,3-c]pyrazole-5-carboxamide;

Compound (36) [R=4-(4-methyl-piperazinyl-1-yl)phenyl; $R_1$=methyl; $R_2=R_3$=H]: 3-{[4-(4-methylpiperazin-1-yl)benzoyl]amino}-N-[(1R)-1-phenylethyl]-1H-thieno[2,3-c]pyrazole-5-carboxamide;

Compound (16) [R=2-thienyl; $R_1=R_2$=methyl; $R_3$=H]: N-(1-methyl-1-phenylethyl)-3-[(thien-2-ylcarbonyl)amino]-1H-thieno[2,3-c]pyrazole-5-carboxamide.

TABLE I

| Compound | Aurora-2 inhibition $IC_{50}$ (nM) | Cell Antiproliferation $IC_{50}$ (nM) |
|---|---|---|
| Reference compound | 18 | 184 |
| (1) | 5 | 6 |
| (2) | 3 | 23 |
| (3) | 6 | 35 |
| (5) | 9 | 30 |
| (29) | 1 | 2 |
| (36) | 1 | 5 |
| (16) | 3 | 56 |

Surprisingly, the Aurora-2 inhibitory activity of the compounds of the invention resulted to be constantly and markedly superior that that of the Reference compound.
In addition, those same compounds resulted to possess a cell antiproliferative effect significantly superior than that of the Reference compound being tested in the same conditions.

From all of the above, the novel compounds of formula (I) of the invention appear to be endowed with a biological profile, considered as a whole, which is unexpectedly superior than that of the closest compound of WO2004013146 and, hence, are particularly advantageous, in therapy, against proliferative disorders associated with an altered Aurora-2 kinase activity.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route. For example, a suitable dosage adopted for oral administration of a compound of formula (I) may range from about 30 to about 500 mg per dose, from 1 to 5 times daily. In general lower doses will be administered when a parental route is employed. Thus, for example, for intravenous administration a dose in the range, for example, 0.5 mg to 30 mg per kg body weight will be generally used. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim to better illustrate the present invention, without posing any limitation to it, the following examples are now given.

EXPERIMENTAL SECTION

The following HPLC method was used in the analysis of the compounds, as specified in the synthetic examples set forth below. As used herein, the term "Rt" refers to the retention time (minutes) for the compound using the HPLC method specified below.

LC-MS Method

HPLC/MS was performed on a Waters X Terra RP 18 (4.6×50 mm, 3.5 □m) column using a Waters 2790 HPLC system equipped with a 996 Waters PDA detector and a Micromass mod. ZQ single quadrupole mass spectrometer, equipped with an electrospray (ESI) ion source. Mobile phase A was ammonium acetate 5 mM buffer (pH 5.5 with acetic acid/acetonitrile 95:5), and Mobile phase B was water/acetonitrile (5:95). Gradient from 10 to 90% B in 8 minutes, hold 90% B 2 min. UV detection at 220 nm and 254 nm. Flow rate 1 mL/min. Injection volume 10 µl. Full scan, mass range from 100 to 800 amu. Capillary voltage was 2.5 KV; Source temperature was 120° C.; Cone was 10 V. Retention Times (LC-MS Rt) are given in minutes at 220 nm or 254 nm. Mass are given as m/z ratio.

Example 1

4-Cyano-5-(methylthio)thiophene-2-carboxylic acid

Aqueous sodium hydroxide (20% w/w solution, 9 mL) was added to a solution of ethyl 4-cyano-5-(methylthio)thiophene-2-carboxylate (10 g, 44 mmol) in 1,4-dioxane (100 mL) at 5° C.

After stirring for 4 hours at room temperature, water (500 mL) was added to the reaction mixture and the pH was adjusted to about 2.5 by adding 2N solution of aqueous hydrochloric acid. A white solid was separated by filtration, washed with water and dried under vacuum to give 8.5 g of the title compound.

LC-MS: Rt 2.4; $[M+H]^+$200.

Example 2 tert-butyl 4-cyano-5-(methylthio)thiophene-2-carboxylate

A mixture of 4-cyano-5-(methylthio)thiophene-2-carboxylic acid (2.0 g, 10 mmol), benzyltrimethylamonium chloride (2.25 g, 10 mmol), tertbutyl bromide (54 mL, 480 mmol) and anhydrous potassium carbonate (36 g, 260 mmol) in dimethylacetamide (100 mL) was stirred at 60° C. for 6 hours. After cooling, the mixture was diluted with ethyl acetate (400 mL) and washed with water. Organic layer was dried and evaporated under reduced pressure to give a residue which was purified by chromatography (eluent ethyl acetate/n-hexane 3:1) thus yielding 1.5 g of the title compound.

LC-MS: Rt 7.4; $[M+H]^+$256.

Example 3 tert-butyl 4-cyano-5-(methylsulfonyl)thiophene-2-carboxylate

A mixture of tert-butyl 4-cyano-5-(methylthio)thiophene-2-carboxylate (1.4 g, 5.5 mmol) and oxone (14.4 g, 21.5 mmol) in dimethylformamide (100 mL) was stirred at room temperature for 16 hours. The reaction mixture was then poured into ice/water (400 mL) and extracted with ethyl acetate. Organic layer was washed with water, dried over anhydrous sodium sulfate and evaporated to dryness to afford 1.5 g of the title compound.

LC-MS: Rt 6.2; $[M+H]^+$288.

Example 4 tert-butyl 4-cyano-5-hydrazinothiophene-2-carboxylate

A mixture of tert-butyl 4-cyano-5-(methylsulfonyl) thiophene-2-carboxylate (2.0 g, 7.0 mmol) and hydrazine hydrate (1.7 mL) in methyl alcohol (30 mL) was stirred at 60° C. for 2 hours. The reaction mixture was diluted with ethyl acetate (100 mL) and washed with water. Organic layer was separated, dried over anhydrous sodium sulfate and evaporated. Through chromatography purification (n-hexane/ethyl acetate 3:2), 1 g of the title compound was thus obtained.

LC-MS: Rt 5.6; $[M+H]^+$240.

Example 5 tert-butyl 3-amino-1H-thieno[2,3-c]pyrazole-5-carboxylate

A mixture of tert-butyl 4-cyano-5-hydrazinothiophene-2-carboxylate (1.0 g, 4.2 mmol) and hydrochloric acid (0.7 mL of a 37% solution) in methyl alcohol (15 mL) was stirred at room temperature for 14 hours. The reaction mixture was diluted with ethyl acetate (50 mL) and washed with an aqueous solution of sodium bicarbonate. Organic layer was separated, dried over anhydrous sodium sulfate and evaporated to afford 0.9 g of the title compound.

LC-MS: Rt 4.5; $[M+H]^+$240.

Example 6

5-tert-butyl 1-ethyl 3-amino-1H-thieno[2,3-c]pyrazole-1,5-dicarboxylate

A solution of ethyl chlorocarbonate (4.90 mL, 51.7 mmol) in tetrahydrofuran (THF, 60 mL) was slowly added to a mixture of tert-butyl 3-amino-1H-thieno[2,3-c]pyrazole-5-carboxylate (12.0 g, 50.2 mmol) and diisopropylethylamine (DIEA, 51.5 mL, 301 mmol) in THF (300 mL), maintaining the temperature between −5 and −10° C. The reaction was kept at the same temperature for 5 minutes then allowed to reach room temperature. The obtained mixture was evaporated to dryness under vacuum and the residue extracted with ethyl acetate (AcOEt) and water. The organic layer was separated, dried over sodium sulfate and evaporated to dryness. The resulting raw material was triturated with diethyl ether to give 13.7 g of the title compound as a white solid.

LC-MS: Rt 5.6; [M+H]$^+$312.

Example 7

5-tert-butyl 1-ethyl 3-[(4-morpholin-4-ylbenzoyl) amino]-1H-thieno[2,3-c]pyrazole-1,5-dicarboxylate Oxalyl chloride (20.2 mL, 231 mmol) was added to a suspension of 4-morpholin-4-ylbenzoic acid (7.98 g, 38.5 mmol) in dry dichloromethane (DCM, 210 mL) and dimethylformamide (DMF, 0.04 mL). After refluxing the mixture for 6.5 hours, volatiles were carefully removed under reduced pressure (taking up the residue three times with toluene). The resulting 4-morpholin-4-ylbenzoyl chloride hydrochloride was added portion-wise (in about 0.5 hours) to a suspension of 5-tert-butyl 1-ethyl 3-amino-1H-thieno[2,3-c]pyrazole-1, 5-dicarboxylate (6.0 g, 19.3 mmol) in dry DCM (200 mL) and pyridine (23.2 mL, 289 mmol), under stirring at 5° C. The resulting suspension was stirred for 20 hours at room temperature. 300 mL of DCM and 300 mL of aqueous sodium bicarbonate were then added to the reaction mixture; the organic layer was separated, washed with brine, dried over sodium sulphate and evaporated. Purification by chromatography (DCM/ethyl acetate 7:3) gave 4.05 g of the title compound.

LC-MS: Rt 7.2; [M+H]$^+$501.

By operating in an analogous way and by reacting 5-tert-butyl 1-ethyl 3-amino-1H-thieno[2,3-c]pyrazole-1,5-dicarboxylate with the appropriate acyl chloride derivative, the following compounds were thus prepared:

5-tert-butyl 1-ethyl 3-{[4-(4-methylpiperazin-1-yl)benzoyl] amino}-1H-thieno[2,3-c]pyrazole-1,5-dicarboxylate;
5-tert-butyl 1-ethyl 3-[(4-fluorobenzoyl)amino]-1H-thieno [2,3-c]pyrazole-1,5-dicarboxylate;
5-tert-butyl 1-ethyl 3-[(thien-2-ylcarbonyl)amino]-1H-thieno[2,3-c]pyrazole-1,5-dicarboxylate;
5-tert-butyl 1-ethyl 3-{[(1-methyl-1H-pyrrol-2-yl)carbonyl] amino}-1H-thieno[2,3-c]pyrazole-1,5-dicarboxylate;
5-tert-butyl 1-ethyl 3-(2-furoylamino)-1H-thieno[2,3-c] pyrazole-1,5-dicarboxylate;
5-tert-butyl 1-ethyl 3-({4-[(1-methylpiperidin-4-yl)oxy] benzoyl}amino)-1H-thieno[2,3-c]pyrazole-1,5-dicarboxylate;
5-tert-butyl 1-ethyl 3-({4-[(4-methylpiperazin-1-yl)methyl] benzoyl}amino)-1H-thieno[2,3-c]pyrazole-1,5-dicarboxylate.

Example 8

1-(ethoxycarbonyl)-3[(4-morpholin-4-ylbenzoyl) amino]-1H-thieno[2,3-c]pyrazole-5-carboxylic acid hydrochloride 5-tert-butyl 1-ethyl 3-[(4-morpholin-4-ylbenzoyl)amino]-1H-thieno[2,3-c]pyrazole-1,5-dicarboxylate (4.05 g) was added to a solution of hydrochloric acid in dioxane (88 mL, 4N solution). The resulting mixture was stirred at room temperature for 72 hours. Afterward, volatiles were removed by evaporation under reduced pressure and the residue triturated with diethyl ether, filtered, extensively washed with diethyl ether and dried under vacuum at 40° C. to give 3.4 g of the title compound, used in the next step without further purification.

LC-MS: Rt 3.1; [M+H]$^+$445.

By operating as above reported and by starting from the suitable intermediate compound, the following derivatives were analogously prepared:

1-(ethoxycarbonyl)-3-{[4-(4-methylpiperazin-1-yl)benzoyl] amino}-1H-thieno[2,3-c]pyrazole-5-carboxylic acid hydrochloride;
1-(ethoxycarbonyl)-3-[(4-fluorobenzoyl)amino]-1H-thieno [2,3-c]pyrazole-5-carboxylic acid;
1-(ethoxycarbonyl)-3-[(thien-2-ylcarbonyl)amino]-1H-thieno[2,3-c]pyrazole-5-carboxylic acid;
1-(ethoxycarbonyl)-3-{[(1-methyl-1H-pyrrol-2-yl)carbonyl]amino}-1H-thieno[2,3-c]pyrazole-5-carboxylic acid;
1-(ethoxycarbonyl)-3-(2-furoylamino)-1H-thieno[2,3-c] pyrazole-5-carboxylic acid;
1-(ethoxycarbonyl)-3-({4-[(1-methylpiperidin-4-yl)oxy] benzoyl}amino)-1H-thieno[2,3-c]pyrazole-5-carboxylic acid hydrochloride;
1-(ethoxycarbonyl)-3-({4-[(4-methylpiperazin-1-yl)methyl] benzoyl}amino)-1H-thieno[2,3-c]pyrazole-5-carboxylic acid hydrochloride.

Example 9 ethyl 5-{[(1-methyl-1-phenylethyl)amino]carbonyl}-3-[(4-morpholin-4-ylbenzoyl)amino]-1H-thieno[2,3-c]pyrazole-1-carboxylate A mixture of cumylamine (1.43 g, 10.6 mmol), 2-(1H-benzotriazol-1-yl)-1,1,3,3-tetramethyluronium tetrafluoroborate (TBTU, 3.40 g, 10.6 mmol), 1-(ethoxycarbonyl)-3-[(4-morpholin-4-ylbenzoyl)amino]-1H-thieno[2,3-c] pyrazole-5-carboxylic acid hydrochloride (3.40 mg, 7.07 mmol) and N,N'-diisopropylethylamine (12.1 mL, 7.07 mmol) in 80 mL of dimethylformamide was stirred at room temperature for 20 hours. Afterward the reaction mixture was diluted with water and extracted with dichloromethane. Volatiles were removed by evaporation under reduced pressure and the residue was triturated with ethyl acetate, filtered, extensively washed with diethyl ether and dried under vacuum at 40° C., to give 3.7 g of the title compound, used in the next step without further purification.

LC-MS: Rt 6.8; [M+H]$^+$562.

By operating as above reported and by starting from the suitable intermediate derivative, the following compounds were analogously prepared:

ethyl 3-[(4-morpholin-4-ylbenzoyl)amino]-5-{[(1-phenylcyclopropyl)amino]carbonyl}-1H-thieno[2,3-c]pyrazole-1-carboxylate;
ethyl 5-({[(1R)-1-(4-fluorophenyl)ethyl]amino}carbonyl)-3-[(4-morpholin-4-ylbenzoyl)amino]-1H-thieno[2,3-c] pyrazole-1-carboxylate;
ethyl 3-[(4-morpholin-4-ylbenzoyl)amino]-5-({[(1R)-1-phenylpropyl]amino}carbonyl)-1H-thieno[2,3-c]pyrazole-1-carboxylate;
ethyl 3-[(4-morpholin-4-ylbenzoyl)amino]-5-({[(1S)-1-phenyl-2-pyrrolidin-1-ylethyl]amino}carbonyl)-1H-thieno[2, 3-c]pyrazole-1-carboxylate;
ethyl 3-[(4-morpholin-4-ylbenzoyl)amino]-5-({[(1S)-2-morpholin-4-yl-1-phenylethyl]amino}carbonyl)-1H-thieno[2,3-c]pyrazole-1-carboxylate;

ethyl 3-[(4-fluorobenzoyl)amino]-5-{[(1-phenylcyclopropyl)amino]carbonyl)-1H-thieno[2,3-c]pyrazole-1-carboxylate;
ethyl 3-[(4-fluorobenzoyl)amino]-54[(1-methyl-1-phenylethyl)amino]carbonyl}-1H-thieno[2,3-c]pyrazole-1-carboxylate;
ethyl 3-[(4-fluorobenzoyl)amino]-5-({[(1R)-1-phenylpropyl]amino}carbonyl)-1H-thieno[2,3-c]pyrazole-1-carboxylate;
ethyl 3-[(4-fluorobenzoyl)amino]-5-({[(1S)-1-phenyl-2-pyrrolidin-1-ylethyl]amino}carbonyl)-1H-thieno[2,3-c]pyrazole-1-carboxylate;
ethyl 3-[(4-fluorobenzoyl)amino]-5-({[(1R)-1-(4-fluorophenyl)ethyl]amino}carbonyl)-1H-thieno[2,3-c]pyrazole-1-carboxylate;
ethyl 3[(4-fluorobenzoyl)amino]-5-({[(1S)-2-morpholin-4-yl-1-phenylethyl]amino}carbonyl)-1H-thieno[2,3-c]pyrazole-1-carboxylate;
ethyl 5-{[(1-ethyl-1-phenylpropyl)amino]carbonyl}-3-[(4-fluorobenzoyl)amino]-1H-thieno[2,3-c]pyrazole-1-carboxylate;
ethyl 3-[(4-fluorobenzoyl)amino]-5-{[(1-phenylcyclopentyl)amino]carbonyl}-1H-thieno[2,3-c]pyrazole-1-carboxylate;
ethyl 5-({[(1S)-2-morpholin-4-yl-1-phenylethyl]amino}carbonyl)-3-[(thien-2-ylcarbonyl)amino]-1H-thieno[2,3-c]pyrazole-1-carboxylate;
ethyl 5-{[(1-methyl-1-phenylethyl)amino]carbonyl}-3-[(thien-2-ylcarbonyl)amino]-1H-thieno[2,3-c]pyrazole-1-carboxylate;
ethyl 5-({[(1R)-1-(4-fluorophenyl)ethyl]amino}carbonyl)-3-[(thien-2-ylcarbonyl)amino]-1H-thieno[2,3-c]pyrazole-1-carboxylate;
ethyl 5-{[(1-phenylcyclopropyl)amino]carbonyl}-3-[(thien-2-ylcarbonyl)amino]-1H-thieno[2,3-c]pyrazole-1-carboxylate;
1-(ethoxycarbonyl)-3-({4-[(4-methylpiperazin-1-yl)methyl]benzoyl}amino)-1H-thieno[2,3-c]pyrazole-5-carboxylic acid hydrochloride;
ethyl 5-({[(1R)-1-phenylpropyl]amino}carbonyl)-3-[(thien-2-ylcarbonyl)amino]-1H-thieno[2,3-c]pyrazole-1-carboxylate;
ethyl 5-{[(1-methyl-1-phenylethyl)amino]carbonyl}-3-{[(1-methyl-1H-pyrrol-2-yl)carbonyl]amino}-1H-thieno[2,3-c]pyrazole-1-carboxylate;
ethyl 3-{[(1-methyl-1H-pyrrol-2-yl)carbonyl]amino}-5-{[(1-phenylcyclopropyl)amino]carbonyl}-1H-thieno[2,3-c]pyrazole-1-carboxylate;
ethyl 3-(2-furoylamino)-5-{[(1-phenylcyclopropyl)amino]carbonyl}-1H-thieno[2,3-c]pyrazole-1-carboxylate;
ethyl 3-(2-furoylamino)-5-{[(1-methyl-1-phenylethyl)amino]carbonyl}-1H-thieno[2,3-c]pyrazole-1-carboxylate;
ethyl 5-{[(1-methyl-1-phenylethyl)amino]carbonyl}-3-({4-[(1-methylpiperidin-4-yl)oxy]benzoyl}amino)-1H-thieno[2,3-c]pyrazole-1-carboxylate;
ethyl 3-({4-[(1-methylpiperidin-4-yl)oxy]benzoyl}amino)-5-{[(1-phenylcyclopropyl)amino]carbonyl}-1H-thieno[2,3-c]pyrazole-1-carboxylate;
ethyl 5-{[(1-methyl-1-phenylethyl)amino]carbonyl}-3-({4-[(4-methylpiperazin-1-yl)methyl]benzoyl}amino)-1H-thieno[2,3-c]pyrazole-1-carboxylate;
ethyl 3-({4-[(4-methylpiperazin-1-yl)methyl]benzoyl}amino)-5-{[(1-phenylcyclopropyl)amino]carbonyl}-1H-thieno[2,3-c]pyrazole-1-carboxylate.

Example 10

N-(1-methyl-1-phenylethyl)-3[(4-morpholin-4-ylbenzoyl)amino]-1H-thieno[2,3-c]pyrazole-5-carboxamide (1)

A suspension of ethyl 5-{[(1-methyl-1-phenylethyl)amino]carbonyl}-3-[(4-morpholin-4-ylbenzoyl)amino]-1H-thieno[2,3-c]pyrazole-1-carboxylate (3.71 g, 6.6 mmol) in methanol (MeOH, 70 mL) and triethylamine (TEA, 7 mL) was stirred at 70° C. for 5 hours. After evaporation of the solvent under reduced pressure, the residue was taken up with DCM and washed with water. The organic layer was separated, dried over sodium sulfate and evaporated. Purification by chromatography (DCM/MeOH 47:3) gave 2.8 g of the title compound.

LC-MS: Rt 5.70; [M+H]$^+$490.

By operating as above reported and by starting from the suitable intermediate derivative, the following compounds were analogously prepared:

2) 3-[(4-morpholin-4-ylbenzoyl)amino]-N-(1-phenylcyclopropyl)-1H-thieno[2,3-c]pyrazole-5-carboxamide; LC-MS: Rt 5.5; [M+H]$^+$488;
3) N-[(1R)-1-(4-fluorophenyl)ethyl]-3-[(4-morpholin-4-ylbenzoyl)amino]-1H-thieno[2,3-c]pyrazole-5-carboxamide; LC-MS: Rt 5.6; [M+H]$^+$494;
4) 3-[(4-morpholin-4-ylbenzoyl)amino]-N-[(1R)-1-phenylpropyl]-1H-thieno[2,3-c]pyrazole-5-carboxamide; LC-MS: Rt 5.8; [M+H]$^+$ 490;
5) 3-[(4-morpholin-4-ylbenzoyl)amino]-N-[(1S)-1-phenyl-2-pyrrolidin-1-ylethyl]-1H-thieno[2,3-c]pyrazole-5-carboxamide; LC-MS: Rt 4.3; [M+H]$^+$545;
6) 3-[(4-morpholin-4-ylbenzoyl)amino]-N-[(1S)-2-morpholin-4-yl-1-phenylethyl]-1H-thieno[2,3-c]pyrazole-5-carboxamide; LC-MS: Rt 5; [M+H]$^+$561;
7) 3-[(4-fluorobenzoyl)amino]-N-(1-phenylcyclopropyl)-1H-thieno[2,3-c]pyrazole-5-carboxamide; LC-MS: Rt 5.7; [M+H]$^+$ 421;
8) 3-[(4-fluorobenzoyl)amino]-N-(1-methyl-1-phenylethyl)-1H-thieno[2,3-c]pyrazole-5-carboxamide; LC-MS: Rt 6.1; [M+H]$^+$423;
9) 3-[(4-fluorobenzoyl)amino]-N-[(1R)-1-phenylpropyl]-1H-thieno[2,3-c]pyrazole-5-carboxamide; LC-MS: Rt 6.1; [M+H]$^+$423;
10) 3-[(4-fluorobenzoyl)amino]-N-[(1S)-1-phenyl-2-pyrrolidin-1-ylethyl]-1H-thieno[2,3-c]pyrazole-5-carboxamide; LC-MS: Rt 4.4; [M+H]$^+$478;
11) 3-[(4-fluorobenzoyl)amino]-N-[(1R)-1-(4-fluorophenyl)ethyl]-1H-thieno[2,3-c]pyrazole-5-carboxamide; LC-MS: Rt 5.9; [M+H]$^+$427;
12) 3-[(4-fluorobenzoyl)amino]-N-[(1S)-2-morpholin-4-yl-1-phenylethyl]-1H-thieno[2,3-c]pyrazole-5-carboxamide; LC-MS: Rt 5.3; [M+H]$^+$494;
13) N-(1-ethyl-1-phenylpropyl)-3-[(4-fluorobenzoyl)amino]-1H-thieno[2,3-c]pyrazole-5-carboxamide; LC-MS: Rt 6.7; [M+H]$^+$451;
14) 3-[(4-fluorobenzoyl)amino]-N-(1-phenylcyclopentyl)-1H-thieno[2,3-c]pyrazole-5-carboxamide; LC-MS: Rt 6.5; [M+H]$^+$449;
15) N-[(1S)-2-morpholin-4-yl-1-phenylethyl]-3-[(thien-2-ylcarbonyl)amino]-1H-thieno[2,3-c]pyrazole-5-carboxamide; LC-MS: Rt 4.55; [M+H]$^+$482;
16) N-(1-methyl-1-phenylethyl)-3-[(thien-2-ylcarbonyl)amino]-1H-thieno[2,3-c]pyrazole-5-carboxamide; LC-MS: Rt 5.64; [M+H]$^+$411;

17) N-[(1R)-1-(4-fluorophenyl)ethyl]-3-[(thien-2-ylcarbonyl)amino]-1H-thieno[2,3-c]pyrazole-5-carboxamide; LC-MS: Rt 5.63; [M+H]$^+$415;

18) N-(1-phenylcyclopropyl)-3-[(thien-2-ylcarbonyl)amino]-1H-thieno[2,3-c]pyrazole-5-carboxamide; LC-MS: Rt 5.43; [M+H]$^+$409;

19) N-[(1S)-1-phenyl-2-pyrrolidin-1-ylethyl]-3-[(thien-2-ylcarbonyl)amino]-1H-thieno[2,3-c]pyrazole-5-carboxamide; LC-MS: Rt 3.83; [M+H]$^+$466;

20) N-[(1R)-1-phenylpropyl]-3-[(thien-2-ylcarbonyl)amino]-1H-thieno[2,3-c]pyrazole-5-carboxamide; LC-MS: Rt 5.81; [M+H]$^+$411;

21) N-(1-methyl-1-phenylethyl)-3-{[(1-methyl-1H-pyrrol-2-yl)carbonyl]amino}-1H-thieno[2,3-c]pyrazole-5-carboxamide; LC-MS: Rt 5.84; [M+H]$^+$408;

22) 3-{[(1-methyl-1H-pyrrol-2-yl)carbonyl]amino}-N-(1-phenylcyclopropyl)-1H-thieno[2,3-c]pyrazole-5-carboxamide; LC-MS: Rt 5.57; [M+H]$^+$406;

23) 3-(2-furoylamino)-N-(1-phenylcyclopropyl)-1H-thieno[2,3-c]pyrazole-5-carboxamide LC-MS: Rt 5.04; [M+H]$^+$ 393;

24) 3-(2-furoylamino)-N-(1-methyl-1-phenylethyl)-1H-thieno[2,3-c]pyrazole-5-carboxamide LC-MS: Rt 5.35; [M+H]$^+$395;

25) N-(1-methyl-1-phenylethyl)-3-({4-[(1-methylpiperidin-4-yl)oxy]benzoyl}amino)-1H-thieno[2,3-c]pyrazole-5-carboxamide; LC-MS: Rt 3.76; [M+H]$^+$518;

26) 3-({4-[(1-methylpiperidin-4-yl)oxy]benzoyl}amino)-N-(1-phenylcyclopropyl)-1H-thieno[2,3-c]pyrazole-5-carboxamide LC-MS: Rt 3.75; [M+H]$^+$516;

27) N-(1-methyl-1-phenylethyl)-3-({4-[(4-methylpiperazin-1-yl)methyl]benzoyl}amino)-1H-thieno[2,3-c]pyrazole-5-carboxamide; LC-MS: Rt 3.8; [M+H]$^+$517;

28) 3-({4-[(4-methylpiperazin-1-yl)methyl]benzoyl}amino)-N-(1-phenylcyclopropyl)-1H-thieno[2,3-c]pyrazole-5-carboxamide. LC-MS: Rt 3.58; [M+H]$^+$ 515.

Example 11 tert-butyl 1-[4-(4-methylpiperazin-1-yl)benzoyl]-3-{[4-(4-methylpiperazin-1-yl)benzoyl]amino}-1H-thieno[2,3-c]pyrazole-5-carboxylate Oxalyl chloride (11 mL, 127 mmol) was added to a suspension of 4-(4-methylpiperazin-1-yl)benzoic acid (4.62 g, 21 mmol) in DCM (150 mL) and DMF (0.15 mL). After refluxing the mixture for 6.5 hours, volatiles were carefully removed under reduced pressure (taking up the residue three times with toluene).

The resulting 4-(4-methylpiperazin-1-yl)benzoyl chloride hydrochloride was added portion-wise (in about 6 hours) to a suspension of tert-butyl 3-amino-1H-thieno[2,3-c]pyrazole-5-carboxylate (0.62 g, 2.6 mmol) in dry DCM (80 mL) and pyridine (3.1 mL, 39 mmol) under stirring at 5° C. The resulting suspension was stirred for 72 hours at room temperature. 300 mL of aqueous sodium bicarbonate were then added to the reaction mixture and the organic layer was separated, washed with brine, dried over sodium sulphate and evaporated. The residue (6.2 g), a mixture of the title compound, of 4-(4-methylpiperazinin-1-yl)benzoic acid and of 4-(4-methylpiperazinin-1-yl)benzoic anhydride, was used in the following example without purification.

Example 12 tert-butyl 3-{[4-(4-methylpiperazin-1-yl)benzoyl]amino}-1H-thieno[2,3-c]pyrazole-5-carboxylate The mixture obtained as described in Example 11 (6.2 g) was treated with MeOH (45 mL) and TEA (5 mL) and stirred at room temperature for 16 hours. Then, the solution was evaporated and the residue was purified by flash chromatography over silica gel (DCM/MeOH/ammonia 7N solution in methyl alcohol 94:5:1) to afford the title compound as a solid (0.500 g).

LC-MS: Rt 4.72, [M+H]$^+$442.

Example 13

3-([4-(4-methylpiperazin-1-yl)benzoyl]amino)-1H-thieno[2,3-c]pyrazole-5-carboxylic acid hydrochloride A mixture of tert-butyl 3-{[4-(4-methylpiperazin-1-yl)benzoyl]amino}-1H-thieno[2,3-c]pyrazole-5-carboxylate (0.50 g, 1.1 mmol) in hydrochloric acid 4M in dioxane (15 mL) was stirred for 16 hours at room temperature. Afterward, volatiles were removed by evaporation under reduced pressure and the residue was triturated with ethyl ether to give 0.496 g of the title compound as a white solid.

LC-MS: Rt (m) 1.85, [M+H]$^+$386.

Example 14

N-(1-methyl-1-phenylethyl)-3-{[4-(4-methylpiperazin-1-yl)benzoyl]amino}-1H-thieno[2,3-c]pyrazole-5-carboxamide (29)

To an ice-cooled suspension of 3-([4-(4-methylpiperazin-1-yl)benzoyl]amino}-1H-thieno[2,3-c]pyrazole-5-carboxylic acid (113 mg, 0.27 mmol) and N,N'-diisopropylethylamine (2.1 mmol, 0.38 mL) in 3 mL of N,N-dimethylformamide were added, dropwise, 0.154 mL of ethylchloroformate (1.6 mmol). After 20 minutes, 1-methyl-1-phenyl-ethylamine (0.302 mL, 2.1 mmol) was added to the obtained solution and the reaction mixture was allowed to warm to room temperature. After 16 hours, the reaction mixture was diluted with dichloromethane and washed with an aqueous solution of sodium bicarbonate. After solvent evaporation the residue was taken up with methyl alcohol (9 mL) and triethylamine (1 mL) and stirred at 40° C. for 2 hours. The reaction mixture was then evaporated to dryness to give an oil, which was purified by flash chromatography over silica gel, using dichloromethane/methanol/ammonia 7N solution in methyl alcohol (93:6:1) as eluent, to afford the title compound as a white solid (61 mg).

LC-MS: Rt 4.14, [M+H]+ 489.

By operating as above reported and by starting from the suitable intermediate derivative, the following compounds were analogously prepared:

30) 3-{[4-(4-methylpiperazin-1-yl)benzoyl]amino}-N-[(1R)-1-phenylpropyl]-1H-thieno[2,3-c]pyrazole-5-carboxamide LC-MS: Rt 4.54; [M+H]$^+$503;

31) 3-{[4-(4-methylpiperazin-1-yl)benzoyl]amino}-N-[(1S)-2-morpholin-4-yl-1-phenylethyl]-1H-thieno[2,3-c]pyrazole-5-carboxamide LC-MS: Rt 3.14; [M+H]$^+$574;

32) 3-{[4-(4-methylpiperazin-1-yl)benzoyl]amino}-N-[(1S)-1-phenyl-2-pyrrolidin-1-ylethyl]-1H-thieno[2,3-c]pyrazole-5-carboxamide LC-MS: 2.56; [M+H]$^+$558;

33) N-(1-ethyl-1-phenylpropyl)-3-{[4-(4-methylpiperazin-1-yl)benzoyl]amino}-1H-thieno[2,3-c]pyrazole-5-carboxamide LC-MS: Rt 4.4; [M+H]+531;
34) 3-{[4-(4-methylpiperazin-1-yl)benzoyl]amino}-N-(1-phenylcyclopentyl)-1H-thieno[2,3-c]pyrazole-5-carboxamide LC-MS: Rt 5.75; [M+H]$^+$529;
35) 3-{[4-(4-methylpiperazin-1-yl)benzoyl]amino}-N-(1-phenylcyclopropyl)-1H-thieno[2,3-c]pyrazole-5-carboxamide LC-MS: Rt 3.47; [M+H]$^+$501;
36) 3-{[4-(4-methylpiperazin-1-yl)benzoyl]amino}-N-[(1R)-1-phenylethyl]-1H-thieno[2,3-c]pyrazole-5-carboxamide LC-MS: Rt 4.54; [M+H]$^+$489.

Example 15

5-tert-butyl 1-ethyl 3-[(4-chloromethyl-benzoyl)amino]-1H-thieno[2,3-c]pyrazole-1,5-dicarboxylate 4-Chloromethylbenzoyl chloride (5.42 g 28.7 mmol) was added to a suspension of tert-butyl 3-amino-1H-thieno[2,3-c]pyrazole-5-carboxylate (5.94 g, 19.1 mmol) in dry DCM (150 mL) and 2,4,6-collidine (6.94 g, 57.3 mmol) under stirring at 20° C. The resulting suspension was stirred for 3 hours at room temperature. 300 mL of aqueous sodium bicarbonate were then added to the reaction mixture and the organic layer was separated, washed with brine, dried over sodium sulphate and evaporated. The residue was triturated with hexane, filtered and dried at 40° C. under vacuum to give 8.3 g of the title compound.
LC-MS: Rt, [M+H]+464.
By operating as above reported and by starting from the suitable intermediate derivative, the following compounds were analogously prepared: ethyl 3-[(4-chloromethyl-benzoyl)amino]-5-{[(1-phenylcyclopropyl)amino]carbonyl}-1H-thieno[2,3-c]pyrazole-1-carboxylate Example 16

1-(ethoxycarbonyl)-3-[(4-chloromethyl-benzoyl)amino]-1H-thieno[2,3-c]pyrazole-5-carboxylic acid 5-tert-butyl 1-ethyl 3-[(4-chloromethyl-benzoyl)amino]-1H-thieno[2,3-c]pyrazole-1,5-dicarboxylate (8.2 g) was added to a solution of hydrochloric acid in dioxane (88 mL, 4N solution). The resulting mixture was stirred at 50° C. for 2 hours. Afterward, volatiles were removed by evaporation under reduced pressure and the residue triturated with diethyl ether, filtered, extensively washed with diethyl ether and dried under vacuum at 40° C. to give 5.7 g of the title compound, used in the next step without further purification.
LC-MS: Rt; [M+H]$^+$408.

Example 17 ethyl 5-{[(1-methyl-1-phenylethyl)amino]carbonyl}-3-[(4-chloromethyl-benzoyl)amino]-1H-thieno[2,3-c]pyrazole-1-carboxylate A mixture of cumylamine (1.43 g, 10.6 mmol), 2-(1H-benzotriazol-1-yl)-1,1,3,3-tetramethyluronium tetrafluoroborate (TBTU, 3.40 g, 10.6 mmol), 1-(ethoxycarbonyl)-3-[(4-chloromethyl-benzoyl)amino]-1H-thieno[2,3-c]pyrazole-5-carboxylic (2.88 mg, 7.07 mmol) and N,N'-diisopropylethylamine (18.2 mL, 10.6 mmol) in 150 mL of dichloromethane was stirred at room temperature for 20 hours. Afterward the reaction mixture was washed with aqueous hydrochloric acid 2N and brine, and dried over sodium sulphate. Volatiles were removed by evaporation under reduced pressure and the residue was triturated with di-ethyl ether, filtered, extensively washed with diethyl ether and dried under vacuum at 40° C., to give 3.3 g of the title compound, used in the next step without further purification.
LC-MS: Rt; [M+H]$^+$408.

Example 18

3-(4-Pyrrolidin-1-ylmethyl-benzoylamino)-1H-thieno[2,3-c]pyrazole-5-carboxylic acid (1-methyl-1-phenyl-ethyl)-amide (37)

Pirrolidine (1.81 mL, 21.8 mmol), was added to a suspension of ethyl 5-{[(1-methyl-1-phenylethyl)amino]carbonyl}-3-[(4-chloromethyl-benzoyl)amino]-1H-thieno[2,3-c]pyrazole-1-carboxylate (3.80 mg, 7.25 mmol) in 100 mL of dry ethanol. And the resulting mixture was stirred at 79° C. for 1 hour. Afterward the volatiles were removed by evaporation under reduced pressure and the residue was purified by chromatography over silica gel (eluant dichloromethane/methyl alcohol/aqueous ammonia 92:8:01) to give 1.2 g of the title compound.
LC-MS: Rt 3.8; [M+H]$^+$488.
By operating as above reported and by starting from the suitable intermediate derivative, the following compounds were analogously prepared:
38) 3-(4-Morpholin-4-ylmethyl-benzoylamino)-1H-thieno[2,3-c]pyrazole-5-carboxylic acid (1-methyl-1-phenyl-ethyl)-amide; LC-MS: Rt 4.4; [M+H]$^+$504.
39) 3-(4-Piperidin-1-ylmethyl-benzoylamino)-1H-thieno[2,3-c]pyrazole-5-carboxylic acid(1-methyl-1-phenyl-ethyl)-amide; LC-MS: Rt 4.9; [M+H]$^+$502.
40) 3-[4-(Isopropylamino-methyl)-benzoylamino]-1H-thieno[2,3-c]pyrazole-5-carboxylic acid (1-methyl-1-phenyl-ethyl)-amide: Rt 4.7; [M+H]$^+$476.
41) 3-[4-(1,1-Dioxo-1-thiomorpholin-4-ylmethyl)-benzoylamino]-1H-thieno[2,3-c]pyrazole-5-carboxylic acid(1-methyl-1-phenyl-ethyl)-amide; Rt 5.1; [M+H]$^+$552.
42) 3-(4-Morpholin-4-ylmethyl-benzoylamino)-1H-thieno[2,3-c]pyrazole-5-carboxylic acid [1-(3-fluoro-phenyl)-1-methyl-ethyl]-amide; Rt 5.4; [M+H]$^+$522.
43) 3-(4-Morpholin-4-ylmethyl-benzoylamino)-1H-thieno[2,3-c]pyrazole-5-carboxylic acid [1-(2-fluoro-phenyl)-1-methyl-ethyl]-amide; [M+H]$^+$522.
44) 3-(4-Morpholin-4-ylmethyl-benzoylamino)-1H-thieno[2,3-c]pyrazole-5-carboxylic acid [1-(4-fluoro-phenyl)-1-methyl-ethyl]-amide; [M+H]$^+$522.
45) 4-{4-[5-(1-Methyl-1-phenyl-ethylcarbamoyl)-1H-thieno[2,3-c]pyrazol-3-ylcarbamoyl]-benzyl}-piperazine-1-carboxylic acid tert-butyl ester; Rt 6.6; [M+H]$^+$603.
46) 3-[4-(4-Fluoro-piperidin-1-ylmethyl)-benzoylamino]-1H-thieno[2,3-cpyrazole-5-carboxylic acid (1-methyl-1-phenyl-ethyl)-amide; Rt 5.5; [M+H]$^+$520.
47) 3-(4-piperazin-1-ylmethyl-benzoylamino)-1H-thieno[2,3-c]pyrazole-5-carboxylic acid (1-methyl-1-phenyl-ethyl)-amide; Rt 4.6; [M+H]$^+$503.
48) 3-(4-Imidazol-1-ylmethyl-benzoylamino)-1H-thieno[2,3-c]pyrazole-5-carboxylic acid (1-methyl-1-phenyl-ethyl)-amide; Rt 4.9; [M+H]$^+$485.
49) 3-(4-Thiazolidin-3-ylmethyl-benzoylamino)-1H-thieno[2,3-c]pyrazole-5-carboxylic acid (1-methyl-1-phenyl-ethyl)-amide; Rt 6.3; [M+H]$^+$506.
50) 3-(4-Pyrrolidin-1-ylmethyl-benzoylamino)-1H-thieno[2,3-c]pyrazole-5-carboxylic acid [1-(3-fluoro-phenyl)-1-methyl-ethyl]-amide; Rt 4.3; [M+H]$^+$506.

51) 3-(4-Piperidin-1-ylmethyl-benzoylamino)-1H-thieno[2,3-c]pyrazole-5-carboxylic acid [1-(3-fluoro-phenyl)-1-methyl-ethyl]-amide; Rt 4.5; [M+H]⁺520.
52) 3-(4-Piperidin-1-ylmethyl-benzoylamino)-1H-thieno[2,3-c]pyrazole-5-carboxylic acid [1-(2-fluoro-phenyl)-1-methyl-ethyl]-amide; [M+H]⁺520.
53) 3-(4-Azetidin-1-ylmethyl-benzoylamino)-1H-thieno[2,3-c]pyrazole-5-carboxylic acid (1-methyl-1-phenyl-ethyl)-amide; Rt 3.7; [M+H]⁺474.
54) 3-(4-Azetidin-1-ylmethyl-benzoylamino)-1H-thieno[2,3-c]pyrazole-5-carboxylic acid [1-(2-fluoro-phenyl)-1-methyl-ethyl]-amide; [M+H]⁺492.
55) 3-(4-Azetidin-1-ylmethyl-benzoylamino)-1H-thieno[2,3-c]pyrazole-5-carboxylic acid [1-(3-fluoro-phenyl)-1-methyl-ethyl]-amide; [M+H]⁺492.
56) 3-(4-Azetidin-1-ylmethyl-benzoylamino)-1H-thieno[2,3-c]pyrazole-5-carboxylic acid [1-(4-fluoro-phenyl)-1-methyl-ethyl]-amide; [M+H]⁺492.
57) 3-[4-(4-tert-Butyl-piperazin-1-ylmethyl)-benzoylamino]-1H-thieno[2,3-c]pyrazole-5-carboxylic acid (1-methyl-1-phenyl-ethyl)-amide; Rt 4.4; [M+H]⁺559.
58) 3-(4-Pyrrolidin-1-ylmethyl-benzoylamino)-1H-thieno[2,3-c]pyrazole-5-carboxylic acid [1-(4-fluoro-phenyl)-1-methyl-ethyl]-amide; Rt 4.4; [M+H]⁺506.
59) 3-(4-Piperidin-1-ylmethyl-benzoylamino)-1H-thieno[2,3-c]pyrazole-5-carboxylic acid [1-(4-fluoro-phenyl)-1-methyl-ethyl]-amide; Rt 4.6; [M+H]⁺520.
60) 3-Phenylacetylamino-1H-thieno[2,3-c]pyrazole-5-carboxylic acid (1-methyl-1-phenyl-ethyl)-amide; [M+H]⁺448.
61) 3-(4-Dimethylaminomethyl-benzoylamino)-1H-thieno[2,3-c]pyrazole-5-carboxylic acid (1-methyl-1-phenyl-ethyl)-amide; [M+H]⁺462.
62) 3-(4-Cyclopropylaminomethyl-benzoylamino)-1H-thieno[2,3-c]pyrazole-5-carboxylic acid (1-methyl-1-phenyl-ethyl)-amide; Rt 4.1; [M+H]⁺474.
63) 3-(4-Cyclobutylaminomethyl-benzoylamino)-1H-thieno[2,3-c]pyrazole-5-carboxylic acid (1-methyl-1-phenyl-ethyl)-amide; Rt 4.3; [M+H]⁺488.
64) 3-{4-[(Isopropyl-methyl-amino)-methyl]benzoylamino}-1H-thieno[2,3-c]pyrazole-5-carboxylic acid (1-methyl-1-phenyl-ethyl)-amide; Rt 4.3; [M+H]⁺488.
65) 3-(4-Cyclopentylaminomethyl-benzoylamino)-1H-thieno[2,3-c]pyrazole-5-carboxylic acid (1-methyl-1-phenyl-ethyl)-amide; Rt 4.5; [M+H]⁺502.
66) 3-{4-[(Diisopropylamino)-methyl]-benzoylamino}-1H-thieno[2,3-c]pyrazole-5-carboxylic acid (1-methyl-1-phenyl-ethyl)-amide; Rt 5.1; [M+H]⁺518.
67) 3-(4-Aminomethyl-benzoylamino)-1H-thieno[2,3-c]pyrazole-5-carboxylic acid (1-methyl-1-phenyl-ethyl)-amide; [M+H]⁺434.
68) 3-(4-Pyrrolidin-1-ylmethyl-benzoylamino)-1H-thieno[2,3-c]pyrazole-5-carboxylic acid [1-(2-fluoro-phenyl)-1-methyl-ethyl]-amide; [M+H]⁺506.
69) 3-(4-Pyrrolidin-1-ylmethyl-benzoylamino)-1H-thieno[2,3-c]pyrazole-5-carboxylic acid [1-(2-methoxy-phenyl)-1-methyl-ethyl]-amide; [M+H]⁺518.
70) 3-(4-Pyrrolidin-1-ylmethyl-benzoylamino)-1H-thieno[2,3-c]pyrazole-5-carboxylic acid [1-(3-methoxy-phenyl)-1-methyl-ethyl]-amide; [M+H]⁺518.
71) 3-(4-Pyrrolidin-1-ylmethyl-benzoylamino)-1H-thieno[2,3-c]pyrazole-5-carboxylic acid [1-(4-methoxy-phenyl)-1-methyl-ethyl]-amide; [M+H]⁺518.
72) 3-(4-Piperidin-1-ylmethyl-benzoylamino)-1H-thieno[2,3-c]pyrazole-5-carboxylic acid [1-(4-methoxy-phenyl)-1-methyl-ethyl]-amide; [M+H]⁺532
73) 3-(4-Piperidin-1-ylmethyl-benzoylamino)-1H-thieno[2,3-c]pyrazole-5-carboxylic acid [1-(3-methoxy-phenyl)-1-methyl-ethyl]-amide; [M+H]⁺532.
74) 3-(4-Piperidin-1-ylmethyl-benzoylamino)-1H-thieno[2,3-c]pyrazole-5-carboxylic acid [1-(2-methoxy-phenyl)-1-methyl-ethyl]-amide; [M+H]⁺532.
75) 3-(4-Azetidin-1-ylmethyl-benzoylamino)-1H-thieno[2,3-c]pyrazole-5-carboxylic acid [1-(2-methoxy-phenyl)-1-methyl-ethyl]-amide; [M+H]⁺504.
76) 3-(4-Azetidin-1-ylmethyl-benzoylamino)-1H-thieno[2,3-c]pyrazole-5-carboxylic acid [1-(3-methoxy-phenyl)-1-methyl-ethyl]-amide; [M+H]⁺504
77) 3-(4-Azetidin-1-ylmethyl-benzoylamino)-1H-thieno[2,3-c]pyrazole-5-carboxylic acid [1-(4-methoxy-phenyl)-1-methyl-ethyl]-amide; [M+H]⁺504.
78) 3-(4-Morpholin-4-ylmethyl-benzoylamino)-1H-thieno[2,3-c]pyrazole-5-carboxylic acid [1-(4-methoxy-phenyl)-1-methyl-ethyl]-amide; [M+H]⁺534.
79) 3-(4-Morpholin-4-ylmethyl-benzoylamino)-1H-thieno[2,3-c]pyrazole-5-carboxylic acid [1-(3-methoxy-phenyl)-1-methyl-ethyl]-amide; [M+H]⁺534.
80) 3-(4-Morpholin-4-ylmethyl-benzoylamino)-1H-thieno[2,3-c]pyrazole-5-carboxylic acid [1-(2-methoxy-phenyl)-1-methyl-ethyl]-amide; [M+H]⁺534
81) 3-[4-(4-Methyl-piperazin-1-yl)-benzoylamino]-1H-thieno[2,3-c]pyrazole-5-carboxylic acid [1-methyl-1-(2-methoxy-phenyl)-ethyl]-amide; [M+H]⁺547.
82) 3-[4-(4-Methyl-piperazin-1-yl-benzoylamino]-1H-thieno[2,3-c]pyrazole-5-carboxylic acid [1-methyl-1-(3-methoxy-phenyl)-ethyl]-amide; [M+H]⁺547.
83) 3-[4-(4-Methyl-piperazin-1-yl)-benzoylamino]-1H-thieno[2,3-c]pyrazole-5-carboxylic acid [1-methyl-1-(4-methoxy-phenyl)-ethyl]-amide; [M+H]⁺547.
84) 3-[4-(4-Methyl-piperazin-1-yl)-benzoylamino]-1H-thieno[2,3-c]pyrazole-5-carboxylic acid [1-methyl-1-(2-fluoro-phenyl)-ethyl]-amide; [M+H]⁺535.
85) 3-[4-(4-Methyl-piperazin-1-yl)-benzoylamino]-1H-thieno[2,3-c]pyrazole-5-carboxylic acid [1-methyl-1-(3-fluoro-phenyl)-ethyl]-amide; [M+H]⁺535.
86) 3-[4-(4-Methyl-piperazin-1-yl)-benzoylamino]-1H-thieno[2,3-c]pyrazole-5-carboxylic acid [1-methyl-1-(4-fluoro-phenyl)-ethyl]-amide; [M+H]⁺535.
87) 3-({4-[(1-methylpiperidin-4-yl)oxy]benzoyl}amino)-1H-thieno[2,3-c]pyrazole-5-carboxylic acid [1-methyl-1-(2-fluoro-phenyl)-ethyl]-amide; [M+H]⁺536.
88) 3-({4-[(1-methylpiperidin-4-yl)oxy]benzoyl}amino)-1H-thieno[2,3-c]pyrazole-5-carboxylic acid [1-methyl-1-(3-fluoro-phenyl)-ethyl]-amide; [M+H]⁺536.
89) 3-({4-[(1-methylpiperidin-4-yl)oxy]benzoyl}amino)-1H-thieno[2,3-c]pyrazole-5-carboxylic acid [1-methyl-1-(4-fluoro-phenyl)-ethyl]-amide; [M+H]⁺536.
90) 3-({4-[(1-methylpiperidin-4-yl)oxy]benzoyl}amino)-1H-thieno[2,3-c]pyrazole-5-carboxylic acid [1-methyl-1-(4-methoxy-phenyl)-ethyl]-amide; [M+H]⁺548.
91) 3-({4-[(1-methylpiperidin-4-yl)oxy]benzoyl}amino)-1H-thieno[2,3-c]pyrazole-5-carboxylic acid [1-methyl-1-(3-methoxy-phenyl)-ethyl]-amide; [M+H]⁺548.
92) 3-({4-[(1-methylpiperidin-4-yl)oxy]benzoyl}amino)-1H-thieno[2,3-c]pyrazole-5-carboxylic acid [1-methyl-1-(2-methoxy-phenyl)-ethyl]-amide; [M+H]⁺548.
93) 3-(4-Cyclopropylaminomethyl-benzoylamino)-1H-thieno[2,3-c]pyrazole-5-carboxylic acid 1-(2-fluoro-phenyl)-1-methyl-ethyl]-amide; [M+H]⁺492.
94) 3-(4-Cyclopropylaminomethyl-benzoylamino)-1H-thieno[2,3-c]pyrazole-5-carboxylic acid 1-(2-methoxy-phenyl)-1-methyl-ethyl]-amide; [M+H]⁺504.

95) 3-[4-(Isopropylamino-methyl)-benzoylamino]-1H-thieno[2,3-c]pyrazole-5-carboxylic acid 1-(2-fluoro-phenyl)-1-methyl-ethyl]-amide; [M+H]$^+$494.
96) 3-[4-(Isopropylamino-methyl)-benzoylamino]-1H-thieno[2,3-c]pyrazole-5-carboxylic acid 1-(2-methoxy-phenyl)-1-methyl-ethyl]-amide; [M+H]$^+$506.
97) 3-(4-Azepan-1-ylmethyl-benzoylamino)-1H-thieno[2,3-c]pyrazole-5-carboxylic acid (1-methyl-1-phenyl-ethyl)-amide; Rt 4.6; [M+H]$^+$516.
98) 3-(4-Azepan-1-ylmethyl-benzoylamino)-1H-thieno[2,3-c]pyrazole-5-carboxylic acid [1-(2-fluoro-phenyl)-1-methyl-ethyl]-amide; [M+H]$^+$534.
99) 3-(4-Pyrazol-1-ylmethyl-benzoylamino)-1H-thieno[2,3-c]pyrazole-5-carboxylic acid (1-methyl-1-phenyl-ethyl)-amide; Rt 5.0; [M+H]$^+$485.

Example 19

By operating as above reported in Example 10, the following compounds were analogously prepared by starting from the suitable intermediate derivatives:
100) 3-(4-methoxy-benzoylamino)-1H-thieno[2,3-c]pyrazole-5-carboxylic acid (1-methyl-1-phenyl-ethyl)-amide; [M+H]$^+$435.
101) 3-(3-methoxy-benzoylamino)-1H-thieno[2,3-c]pyrazole-5-carboxylic acid (1-methyl-1-phenyl-ethyl)-amide; [M+H]$^+$435.
102) 3-(2-methoxy-benzoylamino)-1H-thieno[2,3-c]pyrazole-5-carboxylic acid (1-methyl-1-phenyl-ethyl)-amide; [M+H]$^+$435.
103) 3-(3-Morpholin-4-yl-benzoylamino)-1H-thieno[2,3-c]pyrazole-5-carboxylic acid (1-methyl-1-phenyl-ethyl)-amide; [M+H]$^+$490.
104) 3-[4-(4-Methyl-piperazin-1-yl)-benzoylamino]-1H-thieno[2,3-c]pyrazole-5-carboxylic acid (1-methyl-1-phenyl-ethyl)-amide; [M+H]$^+$503.
105) 3-(4-Dimethylamino-benzoylamino)-1H-thieno[2,3-c]pyrazole-5-carboxylic acid (1-methyl-1-phenyl-ethyl)-amide; [M+H]$^+$448.
106) 3-[(Furan-3-carbonyl)-amino]-1H-thieno[2,3-c]pyrazole-5-carboxylic acid (1-methyl-1-phenyl-ethyl)-amide; [M+H]$^+$395.
107) 3-[(Thiophene-3-carbonyl)-amino]-1H-thieno[2,3-c]pyrazole-5-carboxylic acid (1-methyl-1-phenyl-ethyl)-amide; [M+H]$^+$411.
108) 3-[(1-Methyl-1H-pyrrole-3-carbonyl)-amino]-1H-thieno[2,3-c]pyrazole-5-carboxylic acid (1-methyl-1-phenyl-ethyl)-amide; [M+H]$^+$408.
109) 3-[(1-Methyl-1H-pyrazole-3-carbonyl)-amino]-1H-thieno[2,3-c]pyrazole-5-carboxylic acid (1-methyl-1-phenyl-ethyl)-amide; [M+H]$^+$409.
110) 3-[(1-Methyl-1H-pyrazole-5-carbonyl)-amino]-1H-thieno[2,3-c]pyrazole-5-carboxylic acid (1-methyl-1-phenyl-ethyl)-amide; [M+H]$^+$409.
111) 3-[(Pyridine-2-carbonyl)-amino]-1H-thieno[2,3-c]pyrazole-5-carboxylic acid (1-methyl-1-phenyl-ethyl)-amide; [M+H]$^+$406.
112) 3-[(Pyridine-3-carbonyl)-amino]-1H-thieno[2,3-c]pyrazole-5-carboxylic acid (1-methyl-1-phenyl-ethyl)-amide; [M+H]$^+$406.
113) 3-[(Pyridine-4-carbonyl)-amino]-1H-thieno[2,3-c]pyrazole-5-carboxylic acid (1-methyl-1-phenyl-ethyl)-amide; [M+H]$^+$406.
114) 3-(4-Chloro-benzoylamino)-1H-thieno[2,3-c]pyrazole-5-carboxylic acid (1-methyl-1-phenyl-ethyl)-amide; [M+H]$^+$439.
115) -(4-Phenoxy-benzoylamino)-1H-thieno[2,3-c]pyrazole-5-carboxylic acid (1-methyl-1-phenyl-ethyl)-amide; [M+H]$^+$497.
116) 3-(4-Morpholin-4-yl-benzoylamino)-1H-thieno[2,3-c]pyrazole-5-carboxylic acid [1-(2-methoxy-phenyl)-1-methyl-ethyl]-amide; [M+H]$^+$520.
117) 3-(4-Morpholin-4-yl-benzoylamino)-1H-thieno[2,3-c]pyrazole-5-carboxylic acid [1-(4-methoxy-phenyl)-1-methyl-ethyl]-amide; [M+H]$^+$520.
118) 3-[4-(4-Methyl-piperazin-1-yl)-benzoylamino]-1H-thieno[2,3-c]pyrazole-5-carboxylic acid[1-(2-methoxy-phenyl)-1-methyl-ethyl]amide; [M+H]$^+$533.
119) 3-[4-(4-Methyl-piperazin-1-yl)-benzoylamino]-1H-thieno[2,3-c]pyrazole-5-carboxylic acid[1-(3-methoxy-phenyl)-1-methyl-ethyl]-amide; [M+H]$^+$533.
120) 3-[4-(4-Methyl-piperazin-1-yl)-benzoylamino]-1H-thieno[2,3-c]pyrazole-5-carboxylic acid[1-(4-methoxy-phenyl)-1-methyl-ethyl]amide; [M+H]$^+$533.
121) 3-[(Thiophene-2-carbonyl)-amino]-1H-thieno[2,3-c]pyrazole-5-carboxylic acid (1-ethyl-1-phenyl-propyl)-amide; Rt 6.5; [M+H]$^+$439.
122) 3-[(Thiophene-2-carbonyl)-amino]-1H-thieno[2,3-c]pyrazole-5-carboxylic acid (1-phenyl-cyclopentyl)-amide; Rt 6.3; [M+H]$^+$437.
123) 3-[(Thiophene-2-carbonyl)-amino]-1H-thieno[2,3-c]pyrazole-5-carboxylic acid [1-(2-fluoro-phenyl)-1-methyl-ethyl]-amide; Rt 5.7; [M+H]$^+$429.
124) 3-[(Thiophene-2-carbonyl)-amino]-1H-thieno[2,3-c]pyrazole-5-carboxylic acid [1-(3-fluoro-phenyl)-1-methyl-ethyl]-amide; Rt 5.6; [M+H]$^+$429.
125) 3-(4-Trifluoromethoxy-benzoylamino)-1H-thieno[2,3-c]pyrazole-5-carboxylic acid ((S)-2-morpholin-4-yl-1-phenyl-ethyl)-amide; Rt 5.61; [M+H]$^+$560.
126) 3-[4-(2-Dimethylamino-ethoxy)-benzoylamino]-1H-thieno[2,3-c]pyrazole-5-carboxylic acid [1-(2-fluoro-phenyl)-1-methyl-ethyl]-amide; [M+H]$^+$510.
127) 3-[4-(2-Dimethylamino-ethoxy)-benzoylamino]-1H-thieno[2,3-c]pyrazole-5-carboxylic acid (1-methyl-1-phenyl-ethyl)-amide; [M+H]$^+$492.
128) 3-(4-Fluoro-benzoylamino)-1H-thieno[2,3-c]pyrazole-5-carboxylic acid ((S)-1-phenyl-2-piperidin-1-yl-ethyl)-amide; Rt 4.7; [M+H]$^+$492.
129) 3-(4-Morpholin-4-yl-benzoylamino)-1H-thieno[2,3-c]pyrazole-5-carboxylic acid (1-ethyl-1-phenyl-propyl)-amide; Rt 6.4; 518.
130) 3-[(Thiophene-2-carbonyl)-amino]-1H-thieno[2,3-c]pyrazole-5-carboxylic acid ((S)-1-phenyl-2-piperidin-1-yl-ethyl)-amide; Rt 4.4; [M+H]$^+$480.
131) 3-(4-Morpholin-4-yl-benzoylamino)-1H-thieno[2,3-c]pyrazole-5-carboxylic acid (1-phenyl-cyclopentyl)-amide; Rt 6.1; [M+H]$^+$516.
132) 3-[4-(4-Methyl-piperazin-1-yl)-benzoylamino]-1H-thieno[2,3-c]pyrazole-5-carboxylic acid[1-(3-chloro-phenyl)-1-methyl-ethyl]amide; Rt 4.8; [M+H]$^+$537.
133) 3-(4-Fluoro-benzoylamino)-1H-thieno[2,3-c]pyrazole-5-carboxylic acid [1-(3-chloro-phenyl)-1-methyl-ethyl]amide; Rt 6.3; [M+H]$^+$457.
134) 3-(4-Methoxy-benzoylamino)-1H-thieno[2,3-c]pyrazole-5-carboxylic acid (1-phenyl-cyclopropyl)-amide; Rt 5.5; [M+H]$^+$433.
135) 3-(4-Trifluoromethoxy-benzoylamino)-1H-thieno[2,3-c]pyrazole-5-carboxylic acid (1-phenyl-cyclopropyl)-amide; Rt 6.5; [M+H]$^+$487.
136) 3-[(6-Morpholin-4-yl-pyridine-3-carbonyl)-amino]-1H-thieno[2,3-c]pyrazole-5-carboxylic acid (1-methyl-1-phenyl-ethyl)-amide; Rt 5.2 [M+H]$^+$491.

137) 3-(4-Morpholin-4-yl-benzoylamino)-1H-thieno[2,3-c]pyrazole-5-carboxylic acid ((S)-1-methyl-2-morpholin-4-yl-1-phenyl-ethyl)-amide; Rt 5.5 [M+H]$^+$575.

138) 3-(4-Morpholin-4-yl-benzoylamino)-1H-thieno[2,3-c]pyrazole-5-carboxylic acid (1-methyl-1-pyridin-4-yl-ethyl)-amide; Rt 4.4 [M+H]$^+$491.

139) 3-[4-(4-Methyl-piperazin-1-yl)-benzoylamino]-1H-thieno[2,3-c]pyrazole-5-carboxylic acid [1-(4-fluoro-phenyl)-1-methyl-ethyl]amide; Rt 4.3; [M+H]$^+$521.

140) 3-(4-Morpholin-4-yl-benzoylamino)-1H-thieno[2,3-c]pyrazole-5-carboxylic acid [1-(3-methoxy-phenyl)-1-methyl-ethyl]-amide; Rt 5.7; [M+H]$^+$520.

141) 3-[4-(4-Methyl-piperazin-1-yl)-benzoylamino]-1H-thieno[2,3-c]pyrazole-5-carboxylic acid[1-(2-fluoro-phenyl)-1-methyl-ethyl]amide; Rt 4.4; [M+H]$^+$521.

142) 3-[4-(4-Methyl-piperazin-1-yl)-benzoylamino]-1H-thieno[2,3-c]pyrazole-5-carboxylic acid [1-(3-fluoro-phenyl)-1-methyl-ethyl]-amide; Rt 4.5; [M+H]$^+$521.

143) 3-(4-Methanesulfonyl-benzoylamino)-1H-thieno[2,3-c]pyrazole-5-carboxylic acid(1-methyl-1-phenyl-ethyl)-amide; Rt 5.4; [M+H]$^+$483.

144) 3-[4-(1,1-Dioxo-thiomorpholin-4-yl)-benzoylamino]-1H-thieno[2,3-c]pyrazole-5-carboxylic acid (1-methyl-1-phenyl-ethyl)-amide; Rt 4.9 [M+H]$^+$538.

145) 3-(4-Morpholin-4-yl-benzoylamino)-1H-thieno[2,3-c]pyrazole-5-carboxylic acid [1-methyl-1-(3-pyrrolidin-1-yl-phenyl)-ethyl]amide; Rt 6.7; [M+H]$^+$559.

146) 3-[4-(4-Methyl-piperazin-1-yl)-benzoylamino]-1H-thieno[2,3-c]pyrazole-5-carboxylic acid [1-methyl-1-(3-pyrrolidin-1-yl-phenyl)-ethyl]amide; Rt 5.2; [M+H]$^+$572.

147) 3-(4-Morpholin-4-yl-benzoylamino)-1H-thieno[2,3-c]pyrazole-5-carboxylic acid [1-(3-methanesulfonyl-phenyl)-1-methyl-ethyl]amide; Rt 4.6 [M+H]$^+$568.

148) 3-(4-Morpholin-4-yl-benzoylamino)-1H-thieno[2,3-c]pyrazole-5-carboxylic acid [1-(2-fluoro-phenyl)-1-methyl-ethyl]-amide; Rt 5.8; [M+H]$^+$508.

149) 3-(4-Morpholin-4-yl-benzoylamino)-1H-thieno[2,3-c]pyrazole-5-carboxylic acid [1-(3-fluoro-phenyl)-1-methyl-ethyl]-amide; Rt 5.9; [M+H]$^+$508.

150) 3-(4-Morpholin-4-yl-benzoylamino)-1H-thieno[2,3-c]pyrazole-5-carboxylic acid [1-(4-fluoro-phenyl)-1-methyl-ethyl]-amide; Rt 5.9; [M+H]$^+$508.

151) 3-[(Thiophene-2-carbonyl)-amino]-1H-thieno[2,3-c]pyrazole-5-carboxylic acid [1-(4-fluoro-phenyl)-1-methyl-ethyl]-amide; Rt 5.7; [M+H]$^+$429.

152) 3-[(Thiophene-2-carbonyl)-amino]-1H-thieno[2,3-c]pyrazole-5-carboxylic acid [1-(2-methoxy-phenyl)-1-methyl-ethyl]-amide; [M+H]$^+$441.

153) 3-[(Thiophene-2-carbonyl)-amino]-1H-thieno[2,3-c]pyrazole-5-carboxylic acid [1-(3-methoxy-phenyl)-1-methyl-ethyl]-amide; [M+H]$^+$441.

154) 3-[(Thiophene-2-carbonyl)-amino]-1H-thieno[2,3-c]pyrazole-5-carboxylic acid [1-(4-methoxy-phenyl)-1-methyl-ethyl]-amide; [M+H]$^+$441.

155) 3-[(Furan-2-carbonyl)-amino]-1H-thieno[2,3-c]pyrazole-5-carboxylic acid 1-(2-fluoro-phenyl)-1-methyl-ethyl]-amide; [M+H]$^+$413.

156) 3-[(Furan-2-carbonyl)-amino]-1H-thieno[2,3-c]pyrazole-5-carboxylic acid 1-(3-fluoro-phenyl)-1-methyl-ethyl]-amide; [M+H]$^+$413.

157) 3-[(Furan-2-carbonyl)-amino]-1H-thieno[2,3-c]pyrazole-5-carboxylic acid 1-(4-fluoro-phenyl)-1-methyl-ethyl]-amide; [M+H]$^+$413.

158) 3-[(Furan-2-carbonyl)-amino]-1H-thieno[2,3-c]pyrazole-5-carboxylic acid 1-(2-methoxy-phenyl)-1-methyl-ethyl]-amide; [M+H]$^+$413.

159) 3-[(1-Methyl-1H-pyrazole-5-carbonyl)-amino]-1H-thieno[2,3-c]pyrazole-5-carboxylic acid 1-(2-fluoro-phenyl)-1-methyl-ethyl]-amide; [M+H]$^+$427.

160) 3-[(1-Methyl-1H-pyrazole-5-carbonyl)-amino]-1H-thieno[2,3-c]pyrazole-5-carboxylic acid 1-(2-methoxy-phenyl)-1-methyl-ethyl]-amide; [M+H]$^+$439.

161) 3-[(1-Methyl-1H-pyrazole-5-carbonyl)-amino]-1H-thieno[2,3-c]pyrazole-5-carboxylic acid 1-(4-fluoro-phenyl)-1-methyl-ethyl]-amide; [M+H]$^+$427.

162) 3-[(1-Methyl-1H-pyrazole-2-carbonyl)-amino]-1H-thieno[2,3-c]pyrazole-5-carboxylic acid 1-(2-fluoro-phenyl)-1-methyl-ethyl]-amide; [M+H]$^+$426.

163) 3-[(1-Methyl-1H-pyrazole-2-carbonyl)-amino]-1H-thieno[2,3-c]pyrazole-5-carboxylic acid 1-(2-fluoro-phenyl)-1-methyl-ethyl]-amide; [M+H]$^+$426, 164) 3-[(1-Methyl-1H-pyrazole-2-carbonyl)-amino]-1H-thieno[2,3-c]pyrazole-5-carboxylic acid 1-(2-methoxy-phenyl)-1-methyl-ethyl]-amide; [M+H]$^+$438.

165) 3-(4-Morpholin-4-yl-benzoylamino)-1H-thieno[2,3-c]pyrazole-5-carboxylic acid ((R)-1-phenyl-ethyl)-amide; [M+H]$^+$476.

166) 3-(4-Morpholin-4-yl-benzoylamino)-1H-thieno[2,3-c]pyrazole-5-carboxylic acid ((S)-1-phenyl-ethyl)-amide; [M+H]$^+$476.

167) 3-Benzoylamino-1H-thieno[2,3-c]pyrazole-5-carboxylic acid (1-methyl-1-phenyl-ethyl)-amide; [M+H]$^+$405.

168) 3-(3-Fluoro-benzoylamino)-1H-thieno[2,3-c]pyrazole-5-carboxylic acid (1-methyl-1-phenyl-ethyl)-amide; [M+H]$^+$423.

169) 3-(2-Fluoro-benzoylamino)-1H-thieno[2,3-c]pyrazole-5-carboxylic acid (1-methyl-1-phenyl-ethyl)-amide; [M+H]$^+$423.

Biological Testing Example

The following compounds, screened according to the methods described in the pharmacology section above, were all shown to have IC$_{50}$ values for Aurora-2 inhibition below 20 nM:

Compounds: 1; 2; 3; 4; 5; 6; 7; 8; 9; 11; 15; 16; 17; 18; 19; 20; 21; 22; 23; 24; 25; 27; 29; 30; 31; 32; 33; 34; 35; 36; 37; 38; 39; 40; 41; 42; 46; 47; 48; 49; 50; 51; 53; 57; 58; 59; 62; 63; 64; 65; 122; 123; 124; 126; 131; 132; 134; 136; 137; 138; 139; 140; 141; 142; 143; 144; 147; 148; 149; 150 and 151.

The invention claimed is:

1. A method for treating cell proliferative disorders, the disorder selected from the group consisting of psoriasis, arthritis, glomerulonephritis, post-surgical stenosis, restenosis, benign hyperplasia, ovarian cancer, breast cancer, colon cancer, colorectal cancer, cervical cancer, bone cancer, thyroid cancer and melanoma, the method comprising:

administering to a mammal in need thereof an effective amount of a compound of formula (I)

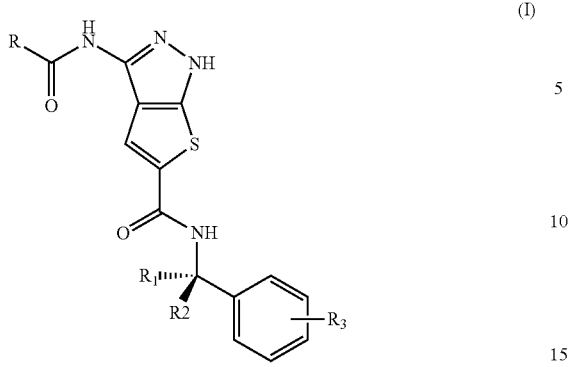

wherein
R is an optionally substituted aryl or heteroaryl group;
$R_1$ and $R_2$ represent, the same or different and independently from each other, a hydrogen atom, a straight or branched $C_1$-$C_3$ alkyl or a group —$CONH_2$ or —$CH_2NR'R''$ or, taken together with the carbon atom to which they are bonded, $R_1$ and $R_2$ may form a $C_3$-$C_6$ cycloalkyl group; with the proviso that compounds of formula (I), when one of $R_1$ and $R_2$ is hydrogen, the other of $R_1$ and $R_2$ is a $C_1$-$C_3$ alkyl and R is 4-(1-methyl-piperazin-4-yl)phenyl, are excluded; R' and R'' represent, the same or different and independently from each other, a hydrogen atom or a straight or branched $C_1$-$C_3$ alkyl group or, taken together with the nitrogen atom to which they are bonded, R' and R'' may form a heterocyclic ring of formula

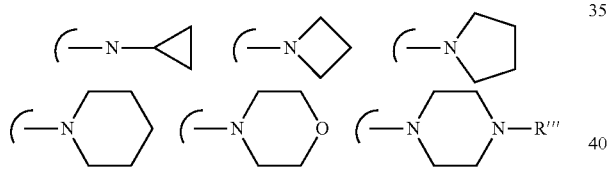

wherein R''' is a hydrogen atom or a straight or branched $C_1$-$C_3$ alkyl group;
$R_3$ is a hydrogen or halogen atom or a group selected from hydroxy, cyano, straight or branched $C_1$-$C_3$ alkyl or $C_1$-$C_3$ alkoxy;
or optical isomers, tautomers and pharmaceutically acceptable salts thereof.

2. The method according to claim 1 further comprising subjecting the mammal in need thereof to a radiation therapy or chemotherapy regimen in combination with at least one cytostatic or cytotoxic agent.

3. The method according to claim 1 wherein the mammal in need thereof is a human.

4. A method for inhibiting Aurora 2 kinase activity which comprises contacting the said kinase with an effective amount of a compound of formula (I)

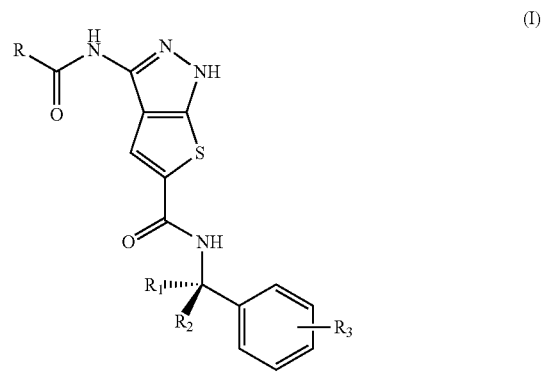

wherein
R is an optionally substituted aryl or heteroaryl group;
$R_1$ and $R_2$ represent, the same or different and independently from each other, a hydrogen atom, a straight or branched $C_1$-$C_3$ alkyl or a group —$CONH_2$ or —$CH_2NR'R''$ or, taken together with the carbon atom to which they are bonded, $R_1$ and $R_2$ may form a $C_3$-$C_6$ cycloalkyl group; with the proviso that compounds of formula (I), when one of $R_1$ and $R_2$ is hydrogen, the other of $R_1$ and $R_2$ is a $C_1$-$C_3$ alkyl and R is 4-(1-methyl-piperazin-4-yl)phenyl, are excluded; R' and R'' represent, the same or different and independently from each other, a hydrogen atom or a straight or branched $C_1$-$C_3$ alkyl group or taken together with the nitrogen atom to which they are bonded, R' and R'' may form a heterocyclic ring of formula

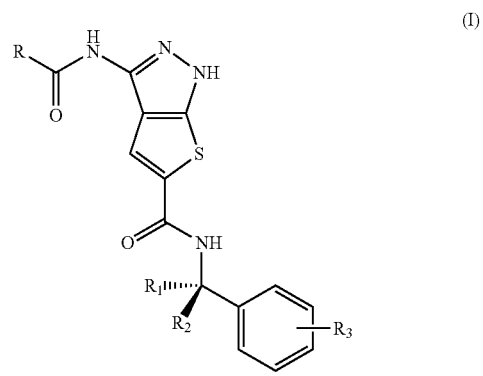

wherein R' is a hydrogen atom or a straight or branched $C_1$-$C_3$ alkyl group,
$R_3$ is a hydrogen or halogen atom or a group selected from hydroxy, cyano, straight or branched $C_1$-$C_3$ alkyl or $C_1$-$C_3$ alkoxy;
or optical isomers, tautomers and pharmaceutically acceptable salts thereof.

* * * * *